United States Patent
Schlegl

(10) Patent No.: US 9,359,412 B2
(45) Date of Patent: Jun. 7, 2016

(54) OPRF/I FUSION PROTEINS, THEIR PREPARATION AND USE

(75) Inventor: Robert Schlegl, Siegenfeld (AT)

(73) Assignee: Valneva Austria GmbH, Vienna (AT)

( * ) Notice: Subject to any disclaimer, the term of this patent is extended or adjusted under 35 U.S.C. 154(b) by 0 days.

(21) Appl. No.: 14/005,579

(22) PCT Filed: Mar. 19, 2012

(86) PCT No.: PCT/EP2012/054783
§ 371 (c)(1),
(2), (4) Date: Oct. 16, 2013

(87) PCT Pub. No.: WO2012/126879
PCT Pub. Date: Sep. 27, 2012

(65) Prior Publication Data
US 2014/0050756 A1    Feb. 20, 2014

Related U.S. Application Data

(60) Provisional application No. 61/454,075, filed on Mar. 18, 2011.

(51) Int. Cl.
| | | |
|---|---|---|
| *A61K 39/00* | (2006.01) | |
| *A61K 39/108* | (2006.01) | |
| *A61K 39/02* | (2006.01) | |
| *C07K 14/21* | (2006.01) | |
| *A61K 39/104* | (2006.01) | |
| *C07K 16/12* | (2006.01) | |

(52) U.S. Cl.
CPC ............... *C07K 14/21* (2013.01); *A61K 39/104* (2013.01); *C07K 16/1214* (2013.01); *C07K 2319/00* (2013.01); *C07K 2319/02* (2013.01); *C07K 2319/21* (2013.01)

(58) Field of Classification Search
CPC ..... A61K 38/00; A61K 38/16; A61K 38/164; A61K 39/00; A61K 39/02; A61K 39/104; A61K 39/395; A61K 39/40
USPC .......... 424/130.1, 139.1, 164.1, 184.1, 185.1, 424/190.1, 234.1, 260.1
See application file for complete search history.

(56) References Cited

U.S. PATENT DOCUMENTS 5,955,090 A * 9/1999 Knapp et al. ................ 424/260.1

FOREIGN PATENT DOCUMENTS

EP         0 717 106 A1    6/1996

OTHER PUBLICATIONS

Baumann et al., Recombinant OprF-OprI as a vaccine against Pseudomonas aeruginosa infections. Vaccine. Feb. 17, 2004;22(7):840-7.

Gabelsberger et al., A hybrid outer membrane protein antigen for vaccination against Pseudomonas aeruginosa. Behring Inst Mitt. Feb. 1997;(98):302-14.

Jang et al., Human immune response to a Pseudomonas aeruginosa outer membrane protein vaccine. Vaccine. Jan. 1999;17(2):158-68.

Kim et al., Comparison of two immunization schedules for a Pseudomonas aeruginosa outer membrane proteins vaccine in burn patients. Vaccine. Dec. 8, 2001;19(9-10):1274-83.

Knapp et al., A recombinant hybrid outer membrane protein for vaccination against Pseudomonas aeruginosa. Vaccine. Mar. 26, 1999;17(13-14):1663-6.

Mansouri et al., Safety and immunogenicity of a Pseudomonas aeruginosa hybrid outer membrane protein F-I vaccine in human volunteers. Infect Immun. Mar. 1999;67(3):1461-70.

Priebe et al., Vaccines for pseudomonas aeruginosa. New bacterial vaccines. 2003;260-82.

Rawling et al., Epitope mapping of the Pseudomonas aeruginosa major outer membrane porin protein OprF. Infect Immun. Jan. 1995;63(1):38-42.

Schiff, Biotechnology products derived from mammalian cell lines: Impact of manufacturing changes. Regulatory Affairs Focus. Oct. 2004: 19-31.

Schuck et al., Determination of the sedimentation coefficient distribution by least-squares boundary modeling. Biopolymers. Oct. 15, 2000;54(5):328-41.

Stanislavsky et al., Clinico-immunological trials of Pseudomonas aeruginosa vaccine. Vaccine. Jul. 1991;9(7):491-4.

Valneva, Press release: update on the Phase II/III efficiency study interim analysis of its Pseudomonas aeruginosa vaccine candidate, Oct. 30, 2013.

Von Specht et al., Immunogenic efficacy of differently produced recombinant vaccines candidates against Pseudomonas aeruginosa infections. J Biotechnol. Sep. 29, 2000;83(1-2):3-12.

(Continued)

*Primary Examiner* — Rodney P Swartz

(74) *Attorney, Agent, or Firm* — Wolf, Greenfield & Sacks, P.C.

(57) ABSTRACT

The present invention relates to a novel trimeric OprF/I fusion protein comprising a portion of the *Pseudomonas aeruginosa* outer membrane protein F which is fused with its carboxy terminal end to a portion of the amino terminal end of the *Pseudomonas aeruginosa* out membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, and further to a novel Opr F/I fusion protein which contains a disulphide bond pattern, preferably selected from the group consisting of (a) Cys18-Cys27-bond, (b) Cys18-Cys27-bond and Cys33-Cys47-bond, and (c) Cys18-Cys47 and Cys27-Cys33-bond, and to immunogenic variants thereof having at least 85% identity to the amino acid sequence of SEQ ID NO: 3. The present invention also relates to a novel method for producing said OprF/I fusion proteins and to their use for the preparation of a pharmaceutical composition and for the preparation of antibodies or antibody derivatives which specifically bind said novel OprF/I fusion proteins.

12 Claims, 10 Drawing Sheets

(56) References Cited

OTHER PUBLICATIONS

Von Specht et al., Protection of immunocompromised mice against lethal infection with Pseudomonas aeruginosa by active or passive immunization with recombinant P. aeruginosa outer membrane protein F and outer membrane protein I fusion proteins. Infect Immun. May 1995;63(5):1855-62.

Worgall et al., Protection against P. aeruginosa with an adenovirus vector containing an OprF epitope in the capsid. J Clin Invest. May 2005;115(5):1281-9. Epub Apr. 1, 2005.

* cited by examiner

SEQUENCE LISTING

```
<160> NUMBER OF SEQ ID NOS: 12

<210> SEQ ID NO 1
<211> LENGTH: 350
<212> TYPE: PRT
<213> ORGANISM: Pseudomonas aeruginosa

<400> SEQUENCE: 1

Met Lys Leu Lys Asn Thr Leu Gly Val Val Ile Gly Ser Leu Val Ala
1               5                   10                  15

Ala Ser Ala Met Asn Ala Phe Ala Gln Gly Gln Asn Ser Val Glu Ile
            20                  25                  30

Glu Ala Phe Gly Lys Arg Tyr Phe Thr Asp Ser Val Arg Asn Met Lys
        35                  40                  45

Asn Ala Asp Leu Tyr Gly Gly Ser Ile Gly Tyr Phe Leu Thr Asp Asp
    50                  55                  60

Val Glu Leu Ala Leu Ser Tyr Gly Glu Tyr His Asp Val Arg Gly Thr
```

```
                65                  70                  75                  80
        Tyr Glu Thr Gly Asn Lys Lys Val His Gly Asn Leu Thr Ser Leu Asp
                        85                  90                  95

Ala Ile Tyr His Phe Gly Thr Pro Gly Val Gly Leu Arg Pro Tyr Val
                        100                 105                 110

Ser Ala Gly Leu Ala His Gln Asn Ile Thr Asn Ile Asn Ser Asp Ser
                        115                 120                 125

Gln Gly Arg Gln Gln Met Thr Met Ala Asn Ile Gly Ala Gly Leu Lys
                    130                 135                 140

Tyr Tyr Phe Thr Glu Asn Phe Phe Ala Lys Ala Ser Leu Asp Gly Gln
        145                 150                 155                 160

Tyr Gly Leu Glu Lys Arg Asp Asn Gly His Gln Gly Glu Trp Met Ala
                        165                 170                 175

Gly Leu Gly Val Gly Phe Asn Phe Gly Gly Ser Lys Ala Ala Pro Ala
                        180                 185                 190

Pro Glu Pro Val Ala Asp Val Cys Ser Asp Ser Asp Asn Asp Gly Val
                        195                 200                 205

Cys Asp Asn Val Asp Lys Cys Pro Asp Thr Pro Ala Asn Val Thr Val
                        210                 215                 220

Asp Ala Asn Gly Cys Pro Ala Val Ala Glu Val Val Arg Val Gln Leu
        225                 230                 235                 240

Asp Val Lys Phe Asp Phe Asp Lys Ser Lys Val Lys Glu Asn Ser Tyr
                        245                 250                 255

Ala Asp Ile Lys Asn Leu Ala Asp Phe Met Lys Gln Tyr Pro Ser Thr
                        260                 265                 270

Ser Thr Thr Val Glu Gly His Thr Asp Ser Val Gly Thr Asp Ala Tyr
                        275                 280                 285

Asn Gln Lys Leu Ser Glu Arg Arg Ala Asn Ala Val Arg Asp Val Leu
                        290                 295                 300

Val Asn Glu Tyr Gly Val Glu Gly Gly Arg Val Asn Ala Val Gly Tyr
        305                 310                 315                 320

Gly Glu Ser Arg Pro Val Ala Asp Asn Ala Thr Ala Glu Gly Arg Ala
                        325                 330                 335

Ile Asn Arg Arg Val Glu Ala Glu Val Glu Ala Glu Ala Lys
                        340                 345                 350

<210> SEQ ID NO 2
<211> LENGTH: 83
<212> TYPE: PRT
<213> ORGANISM: Pseudomonas aeruginosa

<400> SEQUENCE: 2

Met Asn Asn Val Leu Lys Phe Ser Ala Leu Ala Leu Ala Ala Val Leu
1               5                   10                  15

Ala Thr Gly Cys Ser Ser His Ser Lys Glu Thr Glu Ala Arg Leu Thr
                20                  25                  30

Ala Thr Glu Asp Ala Ala Ala Arg Ala Gln Ala Arg Ala Asp Glu Ala
            35                  40                  45

Tyr Arg Lys Ala Asp Glu Ala Leu Gly Ala Ala Gln Lys Ala Gln Gln
        50                  55                  60

Thr Ala Asp Glu Ala Asn Glu Arg Ala Leu Arg Met Leu Glu Lys Ala
65                  70                  75                  80

Ser Arg Lys
```

```
<210> SEQ ID NO 3
<211> LENGTH: 224
<212> TYPE: PRT
<213> ORGANISM: Artificial Sequence
<220> FEATURE:
<223> OTHER INFORMATION: OprF/I fusion protein with N-tag plus Met

<400> SEQUENCE: 3

Met Ala His His His His His Ala Pro Ala Pro Glu Pro Val Ala
1               5                   10                  15

Asp Val Cys Ser Asp Ser Asp Asn Asp Gly Val Cys Asp Asn Val Asp
            20                  25                  30

Lys Cys Pro Asp Thr Pro Ala Asn Val Thr Val Asp Ala Asn Gly Cys
        35                  40                  45

Pro Ala Val Ala Glu Val Val Arg Val Gln Leu Asp Val Lys Phe Asp
    50                  55                  60

Phe Asp Lys Ser Lys Val Lys Glu Asn Ser Tyr Ala Asp Ile Lys Asn
65                  70                  75                  80

Leu Ala Asp Phe Met Lys Gln Tyr Pro Ser Thr Ser Thr Thr Val Glu
                85                  90                  95

Gly His Thr Asp Ser Val Gly Thr Asp Ala Tyr Asn Gln Lys Leu Ser
            100                 105                 110

Glu Arg Arg Ala Asn Ala Val Arg Asp Val Leu Val Asn Glu Tyr Gly
        115                 120                 125

Val Glu Gly Gly Arg Val Asn Ala Val Gly Tyr Gly Glu Ser Arg Pro
    130                 135                 140

Val Ala Asp Asn Ala Thr Ala Glu Gly Arg Ala Ile Asn Arg Arg Val
145                 150                 155                 160

Glu Ser Ser His Ser Lys Glu Thr Glu Ala Arg Leu Thr Ala Thr Glu
                165                 170                 175

Asp Ala Ala Ala Arg Ala Gln Ala Arg Ala Asp Glu Ala Tyr Arg Lys
            180                 185                 190

Ala Asp Glu Ala Leu Gly Ala Ala Gln Lys Ala Gln Gln Thr Ala Asp
        195                 200                 205

Glu Ala Asn Glu Arg Ala Leu Arg Met Leu Glu Lys Ala Ser Arg Lys
    210                 215                 220

<210> SEQ ID NO 4
<211> LENGTH: 223
<212> TYPE: PRT
<213> ORGANISM: Artificial Sequence
<220> FEATURE:
<223> OTHER INFORMATION: OprF/I fusion protein with N-tag without Met

<400> SEQUENCE: 4

Ala His His His His His His Ala Pro Ala Pro Glu Pro Val Ala Asp
1               5                   10                  15

Val Cys Ser Asp Ser Asp Asn Asp Gly Val Cys Asp Asn Val Asp Lys
            20                  25                  30

Cys Pro Asp Thr Pro Ala Asn Val Thr Val Asp Ala Asn Gly Cys Pro
        35                  40                  45

Ala Val Ala Glu Val Val Arg Val Gln Leu Asp Val Lys Phe Asp Phe
    50                  55                  60

Asp Lys Ser Lys Val Lys Glu Asn Ser Tyr Ala Asp Ile Lys Asn Leu
65                  70                  75                  80

Ala Asp Phe Met Lys Gln Tyr Pro Ser Thr Ser Thr Thr Val Glu Gly
                85                  90                  95
```

His Thr Asp Ser Val Gly Thr Asp Ala Tyr Asn Gln Lys Leu Ser Glu
            100                 105                 110

Arg Arg Ala Asn Ala Val Arg Asp Val Leu Val Asn Glu Tyr Gly Val
        115                 120                 125

Glu Gly Gly Arg Val Asn Ala Val Gly Tyr Gly Glu Ser Arg Pro Val
    130                 135                 140

Ala Asp Asn Ala Thr Ala Glu Gly Arg Ala Ile Asn Arg Arg Val Glu
145                 150                 155                 160

Ser Ser His Ser Lys Glu Thr Glu Ala Arg Leu Thr Ala Thr Glu Asp
                165                 170                 175

Ala Ala Ala Arg Ala Gln Ala Arg Ala Asp Glu Ala Tyr Arg Lys Ala
            180                 185                 190

Asp Glu Ala Leu Gly Ala Ala Gln Lys Ala Gln Gln Thr Ala Asp Glu
        195                 200                 205

Ala Asn Glu Arg Ala Leu Arg Met Leu Glu Lys Ala Ser Arg Lys
    210                 215                 220

<210> SEQ ID NO 5
<211> LENGTH: 8
<212> TYPE: PRT
<213> ORGANISM: Artificial Sequence
<220> FEATURE:
<223> OTHER INFORMATION: N-tag plus Met

<400> SEQUENCE: 5

Met Ala His His His His His His
1               5

<210> SEQ ID NO 6
<211> LENGTH: 7
<212> TYPE: PRT
<213> ORGANISM: Artificial Sequence
<220> FEATURE:
<223> OTHER INFORMATION: N-tag without Met

<400> SEQUENCE: 6

Ala His His His His His His
1               5

<210> SEQ ID NO 7
<211> LENGTH: 21
<212> TYPE: PRT
<213> ORGANISM: Escherichia coli

<400> SEQUENCE: 7

Met Lys Lys Thr Ala Ile Ala Ile Ala Val Ala Leu Ala Gly Phe Ala
1               5                   10                  15

Thr Val Ala Gln Ala
            20

<210> SEQ ID NO 8
<211> LENGTH: 24
<212> TYPE: PRT
<213> ORGANISM: Pseudomonas aeruginosa

<400> SEQUENCE: 8

Met Lys Leu Lys Asn Thr Leu Gly Val Val Ile Gly Ser Leu Val Ala
1               5                   10                  15

Ala Ser Ala Met Ala Ala Phe Ala
            20

-continued

```
<210> SEQ ID NO 9
<211> LENGTH: 223
<212> TYPE: PRT
<213> ORGANISM: Artificial Sequence
<220> FEATURE:
<223> OTHER INFORMATION: OprF/I fusion protein with N-tag without Met
<220> FEATURE:
<221> NAME/KEY: DISULFID
<222> LOCATION: (18)..(27)

<400> SEQUENCE: 9

Ala His His His His His Ala Pro Ala Pro Glu Pro Val Ala Asp
1               5                   10                  15

Val Cys Ser Asp Ser Asp Asn Asp Gly Val Cys Asp Asn Val Asp Lys
                20                  25                  30

Cys Pro Asp Thr Pro Ala Asn Val Thr Val Asp Ala Asn Gly Cys Pro
            35                  40                  45

Ala Val Ala Glu Val Val Arg Val Gln Leu Asp Val Lys Phe Asp Phe
        50                  55                  60

Asp Lys Ser Lys Val Lys Glu Asn Ser Tyr Ala Asp Ile Lys Asn Leu
65                  70                  75                  80

Ala Asp Phe Met Lys Gln Tyr Pro Ser Thr Ser Thr Val Glu Gly
                85                  90                  95

His Thr Asp Ser Val Gly Thr Asp Ala Tyr Asn Gln Lys Leu Ser Glu
            100                 105                 110

Arg Arg Ala Asn Ala Val Arg Asp Val Leu Val Asn Glu Tyr Gly Val
        115                 120                 125

Glu Gly Gly Arg Val Asn Ala Val Gly Tyr Gly Glu Ser Arg Pro Val
    130                 135                 140

Ala Asp Asn Ala Thr Ala Glu Gly Arg Ala Ile Asn Arg Arg Val Glu
145                 150                 155                 160

Ser Ser His Ser Lys Glu Thr Glu Ala Arg Leu Thr Ala Thr Glu Asp
                165                 170                 175

Ala Ala Ala Arg Ala Gln Ala Arg Ala Asp Glu Ala Tyr Arg Lys Ala
            180                 185                 190

Asp Glu Ala Leu Gly Ala Ala Gln Lys Ala Gln Gln Thr Ala Asp Glu
        195                 200                 205

Ala Asn Glu Arg Ala Leu Arg Met Leu Glu Lys Ala Ser Arg Lys
    210                 215                 220

<210> SEQ ID NO 10
<211> LENGTH: 223
<212> TYPE: PRT
<213> ORGANISM: Artificial Sequence
<220> FEATURE:
<223> OTHER INFORMATION: OprF/I fusion protein with N-tag without Met
<220> FEATURE:
<221> NAME/KEY: DISULFID
<222> LOCATION: (18)..(27)
<220> FEATURE:
<221> NAME/KEY: DISULFID
<222> LOCATION: (33)..(47)

<400> SEQUENCE: 10

Ala His His His His His Ala Pro Ala Pro Glu Pro Val Ala Asp
1               5                   10                  15

Val Cys Ser Asp Ser Asp Asn Asp Gly Val Cys Asp Asn Val Asp Lys
                20                  25                  30

Cys Pro Asp Thr Pro Ala Asn Val Thr Val Asp Ala Asn Gly Cys Pro
            35                  40                  45
```

-continued

```
Ala Val Ala Glu Val Val Arg Val Gln Leu Asp Val Lys Phe Asp Phe
 50                  55                  60

Asp Lys Ser Lys Val Lys Glu Asn Ser Tyr Ala Asp Ile Lys Asn Leu
 65                  70                  75                  80

Ala Asp Phe Met Lys Gln Tyr Pro Ser Thr Ser Thr Thr Val Glu Gly
                 85                  90                  95

His Thr Asp Ser Val Gly Thr Asp Ala Tyr Asn Gln Lys Leu Ser Glu
            100                 105                 110

Arg Arg Ala Asn Ala Val Arg Asp Val Leu Val Asn Glu Tyr Gly Val
        115                 120                 125

Glu Gly Gly Arg Val Asn Ala Val Gly Tyr Gly Glu Ser Arg Pro Val
130                 135                 140

Ala Asp Asn Ala Thr Ala Glu Gly Arg Ala Ile Asn Arg Arg Val Glu
145                 150                 155                 160

Ser Ser His Ser Lys Glu Thr Glu Ala Arg Leu Thr Ala Thr Glu Asp
                165                 170                 175

Ala Ala Ala Arg Ala Gln Ala Arg Ala Asp Glu Ala Tyr Arg Lys Ala
            180                 185                 190

Asp Glu Ala Leu Gly Ala Ala Gln Lys Ala Gln Gln Thr Ala Asp Glu
        195                 200                 205

Ala Asn Glu Arg Ala Leu Arg Met Leu Glu Lys Ala Ser Arg Lys
210                 215                 220
```

<210> SEQ ID NO 11
<211> LENGTH: 223
<212> TYPE: PRT
<213> ORGANISM: Artificial Sequence
<220> FEATURE:
<223> OTHER INFORMATION: OprF/I fusion protein with N-tag without Met
<220> FEATURE:
<221> NAME/KEY: DISULFID
<222> LOCATION: (18)..(47)
<220> FEATURE:
<221> NAME/KEY: DISULFID
<222> LOCATION: (27)..(33)

<400> SEQUENCE: 11

```
Ala His His His His His Ala Pro Ala Pro Glu Pro Val Ala Asp
 1               5                  10                  15

Val Cys Ser Asp Ser Asp Asn Asp Gly Val Cys Asp Asn Val Asp Lys
                 20                  25                  30

Cys Pro Asp Thr Pro Ala Asn Val Thr Val Asp Ala Asn Gly Cys Pro
             35                  40                  45

Ala Val Ala Glu Val Val Arg Val Gln Leu Asp Val Lys Phe Asp Phe
 50                  55                  60

Asp Lys Ser Lys Val Lys Glu Asn Ser Tyr Ala Asp Ile Lys Asn Leu
 65                  70                  75                  80

Ala Asp Phe Met Lys Gln Tyr Pro Ser Thr Ser Thr Thr Val Glu Gly
                 85                  90                  95

His Thr Asp Ser Val Gly Thr Asp Ala Tyr Asn Gln Lys Leu Ser Glu
            100                 105                 110

Arg Arg Ala Asn Ala Val Arg Asp Val Leu Val Asn Glu Tyr Gly Val
        115                 120                 125

Glu Gly Gly Arg Val Asn Ala Val Gly Tyr Gly Glu Ser Arg Pro Val
130                 135                 140

Ala Asp Asn Ala Thr Ala Glu Gly Arg Ala Ile Asn Arg Arg Val Glu
145                 150                 155                 160
```

```
Ser Ser His Ser Lys Glu Thr Glu Ala Arg Leu Thr Ala Thr Glu Asp
            165                 170                 175

Ala Ala Ala Arg Ala Gln Ala Arg Ala Asp Glu Ala Tyr Arg Lys Ala
            180                 185                 190

Asp Glu Ala Leu Gly Ala Ala Gln Lys Ala Gln Gln Thr Ala Asp Glu
        195                 200                 205

Ala Asn Glu Arg Ala Leu Arg Met Leu Glu Lys Ala Ser Arg Lys
    210                 215                 220

<210> SEQ ID NO 12
<211> LENGTH: 4
<212> TYPE: PRT
<213> ORGANISM: Artificial sequence
<220> FEATURE:
<223> OTHER INFORMATION: synthetic polypeptide

<400> SEQUENCE: 12

Ser Thr Gly Ser
1
```

OPRF/I FUSION PROTEINS, THEIR PREPARATION AND USE

RELATED APPLICATIONS

This application is a national stage filing under 35 U.S.C. §371 of international application PCT/EP2012/054783, filed Mar. 19, 2012, which was published under PCT Article 21(2) in English, and claims the benefit under 35 U.S.C. §119(e) of U.S. provisional application Ser. No. 61/454,075, filed Mar. 18, 2011, the disclosures of which are incorporated by reference herein in their entireties.

FIELD OF THE INVENTION

The present invention relates to a novel trimeric OprF/I fusion protein comprising a portion of the *Pseudomonas aeruginosa* outer membrane protein F which is fused with its carboxy terminal end to a portion of the amino terminal end of the *Pseudomonas aeruginosa* outer membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, and further to a novel OprF/I fusion protein which contains a disulphide bond pattern, preferably selected from the group consisting of (a) Cys18-Cys27-bond, (b) Cys18-Cys27-bond and Cys33-Cys47-bond, and (c) Cys18-Cys47 and Cys27-Cys33-bond, and to immunogenic variants thereof having at least 85% identity to the amino acid sequence of SEQ ID NO: 3. The present invention also relates to a novel method for producing said OprF/I fusion proteins and to their use for the preparation of a pharmaceutical composition and for the preparation of antibodies or antibody derivatives which specifically bind said novel OprF/I fusion proteins.

BACKGROUND OF THE INVENTION

Nosocomial infections are infections that are a result of treatment in a hospital or a healthcare service unit. Infections are considered nosocomial if they first appear 48 hours or more after hospital admission or within 30 days after discharge. This type of infection is also known as a hospital-acquired infection (or, in generic terms, healthcare-associated infection). In the United States, the Center for Disease Control and Prevention estimates that roughly 1.7 million hospital-associated infections, from all types of microorganism, including bacteria, combined, cause or contribute to 99,000 deaths each year. In Europe, where hospital surveys have been conducted, the category of Gram-negative infections are estimated to account for two-thirds of the 25,000 deaths each year. Nosocomial infections can cause severe pneumonia and infections of the urinary tract, bloodstream and other parts of the body. Many types are difficult to attack with antibiotics, and antibiotic resistance is spreading to Gram-negative bacteria that can infect people outside the hospital.

In Gram-negative bacteria, lipopolysaccharides (LPS) and outer-membrane proteins are the major antigenic parts of the bacterial envelope. LPS based vaccines have been extensively studied in the 1970s (Priebe G & Pier G., Vaccines for *Pseudomonas aeruginosa* 2003. New Bacterial vaccines, edited by Elfis R W, Brodeur B. 260-82). Parke Davis produced a vaccine Pseudogen from LPS of 7 different serogroups. Some activity was observed with Pseudogen in non-randomized trials in cancer and burn patients but not in cystic fibrosis (CF) and leukemia patients. Being LPS based Pseudogen was very toxic and therefore not registered (Priebe, supra). Using two different versions of recombinant fusion proteins of Opr's F and I, von Specht and colleagues have shown that active immunization can protect neutropenic mice and passive immunization can protect SCID mice, both against a challenge dose 1000-fold above the LD50 (von Specht, BU et al., Protection of immunocompromised mice against lethal infection with *Pseudomonas aeruginosa* by active or passive immunization with recombinant *Pseudomonas aeruginosa* outer membrane protein F and Outer membrane protein I fusion proteins. Infect Immun 1995; 63(5): 1855-1862; Knapp B et al., A recombinant hybrid outer membrane protein for vaccination against *Pseudomonas aeruginosa*. Vaccine 1999; 17(13-14):1663-1666). Said fusion protein was then tested for safety and immunogenicity in healthy volunteers reaching high levels of specific serum antibodies. To achieve an enhanced mucosal immunogenicity in cystic fibrosis an emulgel formulation of said fusion protein was developed and tested for safety and immunogenicity in healthy volunteers and lung impaired patients. However, the serum antibody response was comparatively low. A systemic i. m. booster has enhanced serum antibody response as compared to solely mucosal vaccination schedule.

An outer membrane protein preparation composed of 4 different strains of *Pseudomonas aeruginosa* with a molecular weight range of 10-100 kDa was developed as a vaccine in Korea. The vaccine contained minimal amounts of polysaccharide and was tested in a double-blind, placebo-controlled trial in burn patients (Jang I I et al., Human immune response to a *Pseudomonas aeruginosa* outer membrane protein vaccine. Vaccine 1999; 17(2): 158-68). Antibody levels to the vaccine antigens rose by 2.3-fold in the placebo group (19 patients) and 4.9 fold in the vaccine group (76 patients) (Kim D K et al., Comparison of two immunization schedules for a *Pseudomonas aeruginosa* outer membrane proteins vaccine in burn patients. Vaccine 2001; 19(9-10):1274-83). Priebe and Pier criticized the study because the follow-up of patients in the trial was incomplete, analysis was not by intention-to-treat, and there were no data regarding clinical outcomes (Priebe, supra). A similar Opr vaccine was tested in Russia 10 years earlier (Stanislaysky E S et al., Clinico-immunological trials of *Pseudomonas aeruginosa* vaccine. Vaccine 1991; 9(7):491-4). *Pseudomonas aeruginosa* vaccine (PV) containing predominantly cell-wall protein protective antigens was tested for safety and immunogenicity by immunization of 119 volunteers. The PV vaccine was well tolerated. A high level of specific antibodies persisted for the 5-month period of observation. The antibody titers increased in 94-97% of volunteers and moreover in 45.6% the antibody titers (the number of ELISA units) increased 2.5-3-fold and more. Anti-*Pseudomonas aeruginosa* plasma was used for the treatment of 46 patients with severe forms of *Pseudomonas aeruginosa* infection (40 adults and six infants aged up to 2 years) and 87% of the patients recovered. There have been no follow-up studies with the PV vaccine after 1991.

Hospital-acquired infections are one of the major causes of death and serious illness worldwide, resulting in an annual cost burden of more than USD 20 billion in the developed world. In the United States and Europe about 6 million patients become infected annually resulting in 140,000 deaths per year. The incidence of nosocomial infections is steadily increasing due to increasing medical interventions and antibiotic resistance. Thus, minimizing risk of mortality through hospital acquired infections by e.g. vaccination of burn victims and fibrosis patients, ICU patients and ventilated ICU patients is and is expected to become even more so a major unmet medical need in said patients.

It has recently been found (U.S. provisional application with application No. 61/426,760) that a vaccine of the above-described hybrid fusion protein comprising the *Pseudomonas aeruginosa* outer membrane protein I (OprI or OMPI) which is fused with its amino terminal end to the carboxy-terminal end of a carboxy-terminal portion of the *Pseudomonas aeruginosa* outer membrane protein F (OprF or OMPF) reduced the mortality rate in mechanically ventilated intensive care patients significantly over alum as placebo control. Mechanically ventilated intensive care patients are at particular risk of acquiring severe and often life-threatening forms of *Pseudomonas aeruginosa* or other infections, such as Ventilator-Associated Pneumonia (VAP), sepsis or soft tissue infection. Such infections also may affect burn victims, severely burned victims, cancer and transplant patients who are immunosuppressed, and cystic fibrosis patients, Intensive Care Unit (ICU) patients or generally all hospitalized patients.

Generally, the expression of soluble OprF/I fusion protein in *E. coli* leads to the formation of non immunological aggregates and misfolded variants. According to Worgall et al. (Worgall S et al., Protection against *P. aeruginosa* with an adenovirus vector containing an OprF epitope in The Capsid., J. of Clinical Investigation, 2005, 115(5), 1281-1289) it is assumed that the native OprF protein has one disulphide bridge from Cys200 to Cys209 of SEQ ID NO: 1 and two free cysteines at Cys215 and Cys229 of SEQ ID NO: 1. In another publication (Rawling E G et al., Epitope Mapping of the *Pseudomonas aeruginosa* Major Outer membrane Protein OprF., Infection and Immunity, 1995, 63 (1), 38-42), however, two disulphide bonds from Cys200 to Cys209 and from Cys215 to Cys229 of SEQ ID NO: 1 are proposed. It cannot be expected that the reported disulphide bond pairing applies to the fusion protein OprF/I since only amino acid No. 190 to amino acid No. 342 of SEQ ID NO: 1 from the native OprF protein are expressed. Since native OprF is an outer membrane protein and contains several transmembrane spans, it is expected that folding in an aqueous environment differs from the folded structure of the natively expressed protein located in a membrane.

In addition, a pharmaceutical composition should be homogenous and stable. Thus, both good manufacturing practice as well as regulatory authority guidelines require that a dosage form of a pharmaceutical or pharmaceutical combination should be in the form of a homogeneous dispersion with respect to the active substances. There is a concern in the field regarding aggregates and a potential for immunogenicity (Leonard J. Schiff, *Biotechnology Products Derived from Mammalian Cell Lines: Impact of Manufacturing Changes* (2004) Regulatory Affairs Focus, October 2004, pages 29-31).

SUMMARY OF THE INVENTION

In accordance with the present invention, it has now surprisingly been found that by a simple reduction and following reoxidation under specific conditions an OprF/I fusion protein variant could be recovered. This specific variant shows a disulfide bond between Cys18 and Cys27 and two free cysteines at positions 33 and 47 (SEQ ID NO: 4) and a trimeric structure which has not been shown before.

Thus, in accordance with the particular findings of the present invention, there is provided:
1. An OprF/I fusion protein comprising a portion of the *Pseudomonas aeruginosa* outer membrane protein F which is fused with its carboxy terminal end to a portion of the amino terminal end of the *Pseudomonas aeruginosa* out membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, and further wherein said fusion protein contains a disulphide bond pattern, preferably selected from the group consisting of (a) Cys18-Cys27-bond (SEQ ID NO: 9), (b) Cys18-Cys27-bond and Cys33-Cys47-bond (SEQ ID NO: 10), and (c) Cys18-Cys47-bond and Cys27-Cys33-bond (SEQ ID NO: 11), or an immunogenic variant thereof having at least 85%, preferably 90%, in particular 95% identity to the amino acid sequence of SEQ ID NO: 4 and the same disulphide bond pattern as specified.
2. A trimeric OprF/I fusion protein comprising a portion of the *Pseudomonas aeruginosa* outer membrane protein F which is fused with its carboxy terminal end to a portion of the amino terminal end of the *Pseudomonas aeruginosa* out membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, or an immunogenic variant thereof having at least 85%, preferably 90%, in particular 95% identity to the amino acid sequence of SEQ ID NO: 4.
3. A method for producing the OprF/I fusion protein as herein described, said method comprising the steps of
   (a) reducing said OprF/I fusion protein with a reducing agent, preferably dithiothreitol (DTT), dithioerythritol (DTE) or β-mercaptoethanol, and
   (b) oxidizing the reduced OprF/I fusion protein with a redox agent, preferably the redox agent glutathione disulfide/glutathione or the redox agent cystine/cysteine, in the presence of a reducing agent, preferably dithiothreitol (DTT), dithioerythritol (DTE) or β-mercaptoethanol.
4. A pharmaceutical composition, in particular a vaccine, comprising said OprF/I hybrid.
5. An antibody or antibody derivative which specifically binds said OprF/I fusion protein.
6. A pharmaceutical composition comprising said antibody or antibody derivative which specifically binds said OprF/I fusion protein.

The invention will now be further illustrated below with the aid of the Figures, Tables, Sequence Listings and Examples, without being restricted hereto.

DETAILED DESCRIPTION OF THE INVENTION

Definitions

The term "about" means a general error range of +/−5%.

The term "immunogenic variant" means a sequence variant of the OprF/I fusion protein which shows in vivo immunogenicity, e.g. in the BALB/c mouse model, e.g. have an ED50 value of 10 µg of lower, more preferably an ED50 value of 5 µg or lower such as e.g. 4 µg or lower, 3 µg or lower or 2 µg or lower (see example section).

The term "binding specificity" or "specifically bind(s)" as used herein refers to the ability of an individual antibody combining site to react with only one antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody. Specific binding between two entities means a binding with an equilibrium constant (KA) of at least $1 \times 10^7 M^{-1}$, $10^8 M^{-1}$, $10^9 M^{-1}$, $10^{10} M^{-1}$, $10^{11} M^{-1}$, $10^{12} M^{-1}$, $10^{13} M^{-1}$. The phrase "specifically (or selectively) binds" to an antibody (e.g., an OprF/I agent-binding antibody) refers to a binding reaction that is determinative of the presence of an antigen (e.g., an OprF/I agent such as a trimer of a mixture of SEQ ID NOs: 9 to 11) in e.g. a heterogeneous population of proteins and other compounds. In addition to the equilibrium constant (KA) noted above, an OprF/I agent-binding antibody of the invention typically also has a dissociation rate constant (Kd) of about $1 \times 10^{-2} s^{-1}$, $1 \times 10^3 s^{-1}$, $1 \times 10^4 s^{-1}$, $1 \times 10^4 s^{-1}$, or lower, and binds to the OprF/I agent such as a trimer of a mixture of SEQ ID NOs: 9 to 11 with an affinity that is at least 2-fold, 5-fold, 10-fold, 20-fold, 50-fold, preferably 100-fold, more preferably 500-fold, or up to 1000-fold or more greater than its affinity for binding to a non-specific antigen. The phrases "an antibody recognizing an antigen" and an antibody specific for an antigen" are used interchangeably herein with the term "an antibody which binds specifically to an antigen".

Specific Aspects of the Invention

According to the present invention the OprF/I fusion protein contains parts of two outer membrane proteins of *Pseudomonas aeruginosa*, $OprF_{190-342}$ and $OprI_{21-83}$, and preferably an N-terminal tag which is in particular useful for the better expression in a suitable host, e.g. *E. coli*, and/or purification of said fusion protein. After expression, OprF/I exists as heterogeneous mixture of misfolded forms (high and low molecular weight aggregates) caused by disulfide scrambling as shown in FIG. 1. Surprisingly, during purification it has been found that after reduction and reoxidation of the fusion protein, novel disulfide bonds were created as shown in FIG. 8 resulting in a separable product mixture of three main products (see FIGS. 7A and 7B, in particular peaks 1, 2 and 3). Unexpectedly, the reoxidized fusion protein or fusion protein mixture is stable and does not form undesired aggregates. Moreover, it was unexpected that one of the three main products corresponding to peak 1 shows the same disulfide bond and two blocked cysteines (caused by covalent reaction with redox-agent (e.g. cysteines) used for reoxidation) as the native, not truncated OprF protein. However, not only this specific fusion protein shows sufficient immunogenicity in vivo but also the other two fusion protein variants corresponding to peaks 2 and 3 (see Table 3), which was indeed unexpected.

Therefore, one aspect of the present invention is directed to said OprF/I fusion protein containing different disulphide bond patterns. Preferably the disulfide bond pattern corresponds to a single Cys18-Cys27-bond according to SEQ ID NO: 9. Another preferred disulphide bond pattern corresponds either to a Cys18-Cys27-bond and a Cys33-Cys47-bond according to SEQ ID NO: 10, or to a Cys18-Cys47-bond and a Cys27-Cys33-bond according to SEQ ID NO: 11.

The described OprF/I fusion protein variants can either separately be isolated or as a mixture with or without further protein components, in particular other fusion protein variants, preferably obtained after the purification process described in the present specification. In case of a mixture of the three main variants (peaks 1-3; FIG. 8), the relative distribution of the variants in the purified mixture analyzed by RP-HPLC are: about 15% to about 18%, preferably about 16%, for the peak 1 variant; about 67% to about 62%, preferably about 66%, for the peak 2 variant; and about 18% to about 20%, preferably about 18%, for the peak 3 variant (FIG. 9). In case of a mixture with further protein components as e.g. shown in FIGS. 7A and 7B, the total relative content or purity of all three main products (peaks 1-3) is at least about 75%, preferably at least about 80% to about 90%, in particular at least about 85%, e.g. 75% to 90% or 85% to 90%. The relative distribution of the three main products in such mixture is the same as described above for a mixture of only the three main products. The specified values can be obtained e.g. by integration of the peak areas obtained by RP-HPLC at 280 and 214 nm.

The present invention also encompasses an immunogenic variant of the described OprF/I fusion protein which has at least 85%, preferably 90%, in particular 95% identity to the amino acid sequence of SEQ ID NO: 3 with the proviso that the specified cysteine residues forming the disulphide bonds are maintained.

In view of the above explanations, a particularly preferred embodiment of the present invention is a mixture, in particular a complex, of OprF/I fusion proteins, each of the OprF/I fusion proteins comprises a portion of the *Pseudomonas aeruginosa* outer membrane protein F which is fused with its carboxy terminal end to a portion of the amino terminal end of the *Pseudomonas aeruginosa* out membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, said mixture containing, in particular in the form of a trimer, (a) an OprF/I fusion protein having only a Cys18-Cys27-bond (SEQ ID NO: 9),
(b) an OprF/I fusion protein having a Cys18-Cys27-bond and a Cys33-Cys47-bond (SEQ ID NO: 10), and/or
(c) an OprF/I fusion protein having a Cys18-Cys47-bond and a Cys27-Cys33-bond (SEQ ID NO: 11).

The amino acid numbering is according to the amino acid sequence of SEQ ID NO: 4. The purity of said mixture is at least about 75%, preferably at least about 80% to about 90%, in particular at least about 85%, e.g. 75% to 90% or 85% to 90% compared to the whole protein content of the mixture as preferably measured by RP-HPLC.

As explained above, a particular advantage of the present invention is that the OprF/I fusion protein does not form undesired aggregates, in particular high molecular weight aggregates, but preferably trimers. Interestingly, the OprF/I fusion protein trimers have a rather elongated shape instead of a globular shape, and a high hydrodynamic radius, in particular with a calculated Stokes-radius of 5.6 nm. The trimer was stable in solution e.g. under physiological conditions such as e.g. pH around 7 and room temperature, i.e. no dissociation was monitored.

Therefore, another aspect of the present invention is a trimeric OprF/I fusion protein comprising a portion of the *Pseudomonas aeruginosa* outer membrane protein F which is fused with its carboxy terminal end to a portion of the amino terminal end of the *Pseudomonas aeruginosa* outer membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, or an immunogenic variant thereof having at least 85%, preferably 90%, in particular 95% identity to the amino acid sequence of SEQ ID NO: 3.

Preferably the trimeric OprF/I fusion protein possesses the same disulfide bonds as explained above. In addition, the trimeric OprF/I fusion protein(s) can be present in a mixture as also explained above.

Another embodiment of the present invention concerns the above-specified OprF/I fusion proteins which additionally contain a N-terminal tag. Therefore, the present invention also concerns a OprF/I fusion protein with 1-24 amino acids fused to its amino terminal end. Preferably the N-terminal tag is selected from Met-, Met-Ala-(His)$_6$- (SEQ ID NO: 5), Ala-(His)$_6$- (SEQ ID NO: 6), Met-Lys-Lys-Thr-Ala-Ile-Ala-Ile-Ala-Val-Ala-Leu-Ala-Gly-Phe-Ala-Thr-Val-Ala-Gln-Ala- (SEQ ID NO: 7), Met-Lys-Leu-Lys-Asn-Thr-Leu-Gly-Val-Val-Ile-Gly-Ser-Leu-Val-Ala-Ala-Ser-Ala-Met-Asn-Ala-Phe-Ala- (SEQ ID NO: 8), or any other N-terminal sequence disclosed in Table 1 of Gabelsberger et al. (1997) (Gabelsberger, J et al., A Hybrid Outer Membrane Protein Antigen for Vaccination Against *Pseudomonas aeruginosa*, Behring Inst. Mitt., 1997, 98, 302-314) namely the *E. coli* OmpT signal peptide or the *E. chrysanthemii* PelB signal peptide. It is also possible that a spacer, preferably a Ser-Thr-Gly-Ser-spacer (SEQ ID NO: 12), between the tag and the N-terminus of the OprF/I fusion protein is located. A particularly preferred OprF/I fusion protein contains an Ala-(His)$_6$-N-terminus (SEQ ID NO: 6) because the fusion protein can easily be purified by immobilized metal affinity chelate chromatography as explained below.

In view of the above explanations, another particularly preferred embodiment of the present invention is, therefore, a mixture, in particular a complex, of OprF/I fusion proteins, each of the OprF/I fusion proteins comprises a portion of the *Pseudomonas aeruginosa* outer membrane protein F which is fused with its carboxy terminal end to a portion of the amino terminal end of the *Pseudomonas aeruginosa* out membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, and each of the OprF/I fusion proteins contains an Ala-(His)$_6$-N-terminus, said mixture containing (a) an OprF/I fusion protein having only a Cys18-Cys27-bond (SEQ ID NO: 9),
(b) an OprF/I fusion protein having a Cys18-Cys27-bond and a Cys33-Cys47-bond (SEQ ID NO: 10), and/or
(c) an OprF/I fusion protein having a Cys18-Cys47-bond and a Cys27-Cys33-bond (SEQ ID NO: 11).

The amino acid numbering is according to the amino acid sequence of SEQ ID NO: 4. The purity of said mixture is at least about 75%, preferably at least about 80% to about 90%, in particular at least about 85%, e.g. 75% to 90% or 85% to 90% compared to the whole protein content of the mixture as preferably measured by RP-HPLC as described above. Furthermore, the mixture contains preferably dimers and in particular trimers of said OprF/I fusion protein.

Another aspect of the present invention concerns a method for producing the above-specified OprF/I fusion protein(s). The preferred method according to the present inventions comprises the steps of (a) reducing said OprF/I fusion protein(s) with a reducing agent, preferably dithiothreitol (DTT), dithioerythritol (DTE) or β-mercaptoethanol, and
(b) oxidizing the reduced OprF/I fusion protein(s) with a redox agent, preferably the redox agent glutathione disulfide/glutathione or the redox agent cystine/cysteine, in the presence of a reducing agent, preferably dithiothreitol (DTT), dithioerythritol (DTE) or β-mercaptoethanol.

The purpose of the reduction step is to break up all intra- and intermolecular disulfide bonds of highly cross-linked disulfide aggregates formed during expression in e.g. *E. coli*. Consequently, the fully reduced protein elutes as a single peak from a RP-HPLC column (see e.g. FIG. 2). The concentration of the reducing agent is in particular from about 3 mM to about 10 mM, preferably from about 3 mM to about 6 mM, e.g. about 5 mM. DTT is the most preferred reducing agent because it is non-toxic. The reaction time of the reduction step (a) is in particular from about 15 minutes to about 2 hours, preferably from about 30 minutes to about 1 hour, especially about 30 minutes, and/or the pH value is preferably from about 7.0 to about 8.5, in particular about 8.0.

The reoxidation can be carried out with different redox systems. The progress of reoxidation, i.e. the formation of disulfide bonds can be monitored by RP-HPLC. Surprisingly it was found that in the presence of reducing and oxidizing agent, in particular at low concentrations, reshuffling of the disulfide bonds resulted in essentially correct bond formation, i.e. misfolded forms of high and low molecular weight aggregates as e.g. shown in FIG. 1 were minimized and a stable solution of immunogenic fusion proteins containing preferably dimers and in particular trimers could be obtained (see e.g. FIGS. 2 and 3). The fusion protein(s) are stable in aqueous solution at neutral pH in the presence of a salt like NaCl, e.g. 0.15 M NaCl, e.g. the fusion protein of SEQ ID NO: 4 in form as a trimer is stable for up to 24 months formulated in PBS at 2 to 8° C. The most preferred redox agent is cystine/cysteine and the most preferred reducing agent in the reoxidation step is DTT. The preferred concentration of the redox agent is from about 0.2 mM to about 4 mM, preferably about 0.2 mM to about 1 mM, in particular about 0.2 mM to about 0.5 mM, and the concentration of the reducing agent is from about 0.5 mM to about 1.5 mM, preferably about 1 mM. The most preferred reoxidation of the fusion protein(s) can be carried out in the presence of 0.5 mM cystine and 1 mM DTT final concentrations. The reaction temperature is in particular from about 18° C. to about 25° C., preferably at about 20° C. The reaction time of the oxidation step (b) is in particular from about 1 hour to about 20 hours, preferably from about 1 hour to about 6 hours, especially from about 1.5 hours to about 2 hours, and/or the pH value is preferably from about 7.5 to about 8.5, in particular about 8.0. Generally, a protein concentration from about 0.2 mg/mL to about 10 mg/mL, preferably from about 0.2 mg/mL to about 1 mg/mL, in particular from about 0.2 mg/mL to about 0.5 mg/mL, especially at about 0.35 mg/mL is applicable.

Another preferred embodiment of the present invention concerns the subsequent purification of the reoxidized fusion protein(s) by an anion exchange chromatography, in particular Diethylaminoethyl- (DEAE-), Diethyl-(2-hydroxypropyl) aminoethyl- (QAE-) or Trimethylaminomethyl- (Q-) exchange chromatography, preferably DEAE- and/or Q-exchange chromatography in order to reduce e.g. the endotoxin content and the genomic DNA content. These remaining impurities can bind to anion exchange media at neutral to slightly basic pH even at higher conductivity, whereas the fusion protein product(s) remain in the flow through. It is most preferred to purify the reoxidized OprF/I fusion protein(s) sequentially by DEAE- and Q-exchange chromatography, preferably by DEAE Sepharose® and Q-Sepharose®-HP chromatography, because the additional chromatography can separate between the various forms of the fusion protein(s), e.g. peak 1, 2, 3, 4, 5, and high molecular weight aggregates, and degradation by-products, e.g. a 7 kD fragment, which still may be present after the reoxidation and the first chromatography purification step. Finally, the purified OprF/I fusion protein(s) can be diafiltrated against a buffer solution, in particular a formulation buffer, e.g. an isotonic phosphate buffer saline solution (pH 7.4).

Generally, the above-described OprF/I fusion protein is produced by fermentation, preferably by expression in a suitable host, e.g. *E. coli*. Usually, the fusion protein is expressed intracellularly in soluble form e.g. at 30° C. and isolated after cell lysis with e.g. lysis buffer containing e.g. high concentrations of a salt, e.g. NaCl, in particular 0.5 M NaCl, and low concentration of a diazole e.g. imidazole, and in particular 0.06 M imidazole. A preferred lysis buffer contains 0.1 M Tris (pH 7.4), 0.5 M NaCl and 0.06 M imidazole.

Thereafter it is preferred to purify the OprF/I fusion protein by affinity chromatography prior to the above-described reduction step. Preferred affinity chromatographies are immunoaffinity or immobilized metal ion affinity chromatography, in particular immobilized metal ion affinity chromatography which can be used for capturing the His-tagged OprF/I fusion protein. Chelating Sepharose® loaded with copper ions is most preferred. Thereafter, desalting e.g. on Sephadex G50 or by ultra/diafiltration using a 100 kDa cut-off membrane is further preferred in order to reduce the content of low molecular weight impurities, e.g. imidazole or copper. In addition, a buffer change is conducted with this purification step. A preferred elution buffer is 0.1 M Tris (pH 8.0) with 0.15M NaCl because this buffer is also a preferred buffer for the following reduction and reoxidation steps. An overview of the most preferred production and purification process is shown in FIG. 6. In short, the process can be summarized as follows:

(a) fermenting a suitable host, e.g. *E. coli*, expressing the described OprF/I fusion protein,
(b) lysing the host,
(c) capturing the produced OprF/I fusion protein by affinity chromatography, preferably by IMAC,
(d) desalting the eluted OprF/I fusion protein,
(e) reducing of the OprF/I fusion protein with a reducing agent,
(f) reoxidizing the reduced OprF/I fusion protein with a redox agent in the presence of a reducing agent,
(g) purifying the reoxidized OprF/I fusion protein on anion exchange chromatography, preferably on DEAE Sepharose®,
(h) purifying the eluted OprF/I fusion protein on a further anion exchange chromatography, preferably on Q-Sepharose®,
(i) diafiltration the eluted OprF/I fusion protein into a formulation buffer.

The formulation buffer is preferably an isotonic salt solution buffer containing, e.g. KCl, NaCl and phosphate buffer (pH 7.4), as in particular specified under the section "Materials".

Consequently, the fusion protein(s) directly obtained by the above-described methods is also a specific embodiment of the present invention. Examples of such fusion protein(s) are also described above and in the following examples.

Another aspect of the present invention is also a pharmaceutical composition, in particular a vaccine, comprising the described OprF/I fusion protein(s) or obtained by the above-described method(s), and optionally at least one additive or adjuvant, in particular aluminium hydroxide, which may serve as an additional stabilizer. A typical formulation of the pharmaceutical composition contains an isotonic phosphate buffer saline solution (pH 7.4).

This preferred composition (SEQ ID NO:4 prepared according to the method described herein and formulated in PBS) is stable up to 24 months at about 2° C. to about 8° C.

Another aspect of the present inventions concerns an antibody or antibody derivative which specifically binds the above-specified OprF/I fusion protein(s) such as e.g. the trimer comprising the herein specified OprF/I fusion protein(s). The antibody is either polyclonal or monoclonal, preferably it is a monoclonal antibody. The term "antibody derivative" is understood as also meaning antigen-binding parts of the inventive antibody, prepared by genetic engineering and optionally modified antibodies, such as, for example, chimeric antibodies, humanized antibodies, multifunctional antibodies, bi- or oligospecific antibodies, single-stranded antibodies, F(ab) or F(ab)$_2$ fragments, which are all well known for a person skilled in the art.

The invention includes isolated antibodies and binding fragments thereof that selectively bind trimers of OprF/I fusion proteins as described herein. As used herein with respect to the binding of trimers of OprF/I fusion proteins by the antibodies and binding fragments, "selectively binds" means that an antibody (binding fragment thereof) preferentially binds to a trimer of OprF/I fusion proteins (e.g., with greater avidity and/or binding affinity) than to an OprF/I fusion protein monomer. In preferred embodiments, the antibodies of the invention and binding fragments thereof bind to a trimer of OprF/I fusion proteins with an avidity and/or binding affinity that is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 500-fold, 1000-fold or more than that exhibited by the antibody and binding fragments thereof for an OprF/I fusion protein monomer. Preferably, the antibody selectively binds trimers of OprF/I fusion proteins, and not OprF/I fusion protein monomers, i.e., substantially exclusively binds to trimers of OprF/I fusion proteins, or specifically binds trimers of OprF/I fusion proteins without substantial binding to OprF/I fusion protein monomers.

In some embodiment, the isolated antibodies or antigen-binding fragments thereof bind to a trimer-specific epitope. Generally, antibodies or antigen-binding fragments thereof that bind to a trimer-specific epitope preferentially bind a trimer of OprF/I fusion proteins rather than a OprF/I fusion protein monomer. To determine if a selected antibody binds preferentially (i.e., selectively and/or specifically) to a trimer of OprF/I fusion proteins, each antibody can be tested in comparative assays (e.g., a surface plasmon resonance (SPR) assay such as BiaCore or immunoprecipitation followed by Western blotting) using trimers of OprF/I fusion proteins and OprF/I fusion protein monomers. A comparison of the results will indicate whether the antibodies bind preferentially to the trimer or to the monomer.

Figure 1:
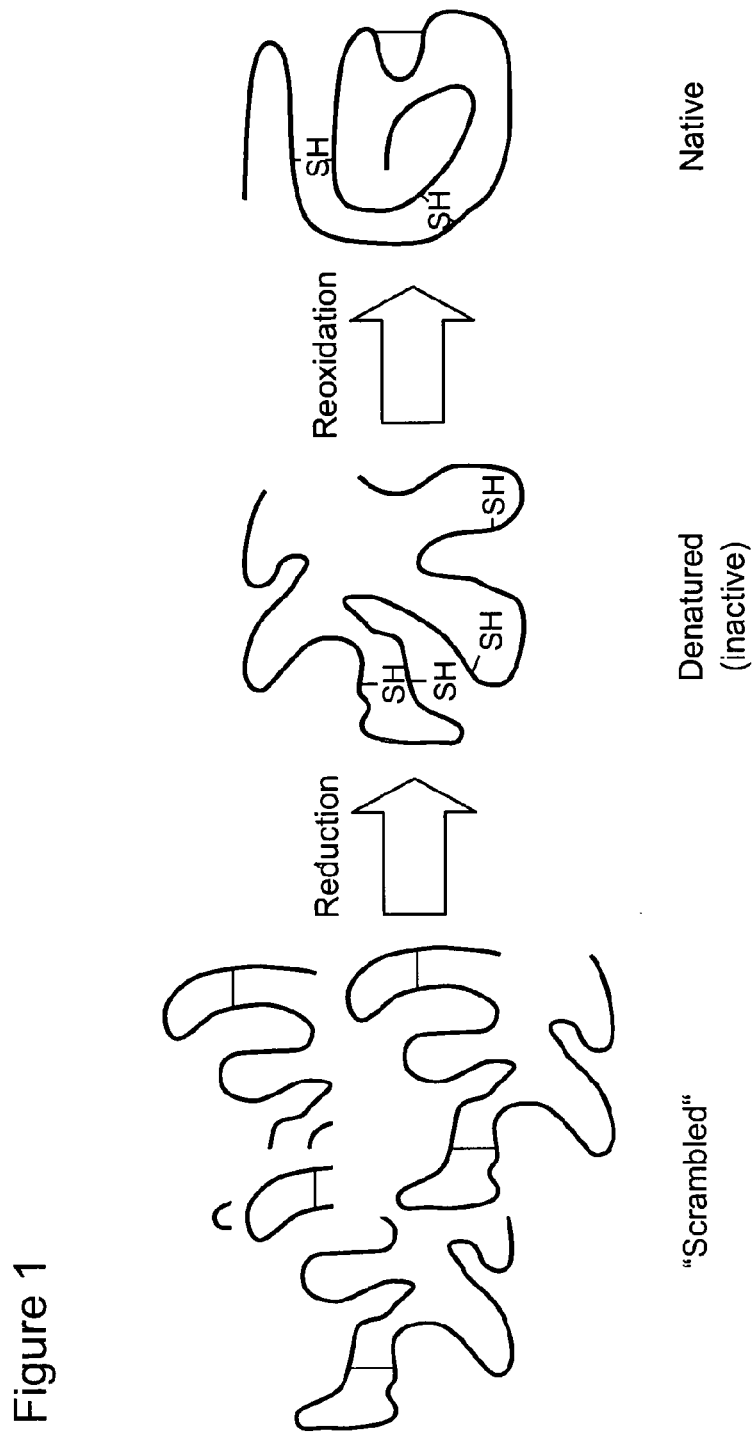
FIG. 1 schematically depicts the reduction and controlled reoxidation processes according to the present invention.

| SEQUENCES |
|---|

SEQ ID NO: 1 (full length Opr F)
  1 MKLKNTLGVV IGSLVAASAM NAFAQGQNSV EIEAFGKRYF TDSVRNMKNA DLYGGSIGYF
 61 LTDDVELALS YGEYHDVRGT YETGNKKVHG NLTSLDAIYH FGTPGVGLRP YVSAGLAHQN
121 ITNINSDSQG RQQMTMANIG AGLKYYFTEN FFAKASLDGQ YGLEKRDNGH QGEWMAGLGV
181 GFNFGGSKAA PAPEPVADVC SDSDNDGVCD NVDKCPDTPA NVTVDANGCP AVAEVVRVQL
241 DVKFDFDKSK VKENSYADIK NLADFMKQYP STSTTVEGHT DSVGTDAYNQ KLSERRANAV
301 RDVLVNEYGV EGGRVNAVGY GESRPVADNA TAEGRAINRR VEAEVEAEAK SEQ ID NO: 2 (precursor Opr I)
  1 MNNVLKFSAL ALAAVLATGC SSHSKETEAR LTATEDAAAR AQARADEAYR KADEALGAAQ
 61 KAQQTADEAN ERALRMLEKA SRK SEQ ID NO: 3 (OprF/I with N-tag plus Met)
  1 MAHHHHHHAP APEPVADVCS DSDNDGVCDN VDKCPDTPAN VTVDANGCPA VAEVVRVQLD
 61 VKFDFDKSKV KENSYADIKN LADFMKQYPS TSTTVEGHTD SVGTDAYNQK LSERRANAVR
121 DVLVNEYGVE GGRVNAVGYG ESRPVADNAT AEGRAINRRV ESSHSKETEA RLTATEDAAA
181 RAQARADEAY RKADEALGAA QKAQQTADEA NERALRMLEK ASRK SEQ ID NO: 4 (OprF/I with N-tag without Met)
  1 AHHHHHHAPA PEPVADVCSD SDNDGVCDNV DKCPDTPANV TVDANGCPAV AEVVRVQLDV
 61 KFDFDKSKVK ENSYADIKNL ADFMKQYPST STTVEGHTDS VGTDAYNQKL SERRANAVRD
121 VLVNEYGVEG GRVNAVGYGE SRPVADNATA EGRAINRRVE SSHSKETEAR LTATEDAAAR
181 AQARADEAYR KADEALGAAQ KAQQTADEAN ERALRMLEKA SRK SEQ ID NO: 5 (N-tag plus Met)
  1 MAHHHHHH SEQ ID NO: 6 (N-tag without Met)
  1 AHHHHHH SEQ ID NO: 7 (OmpA signal peptide E. coli)
  1 MKKTAIAIAV ALAGFATVAQ A SEQ ID NO: 8 (OprF signal peptide P. aeruginosa)
  1 MKLKNTLGVV IGSLVAASAM AAFA SEQ ID NO: 9 (OprF/I with Cys18-Cys27-bond)
Disulfide bond between Cys18 (underlined) and Cys27 (underlined)
  1 AHHHHHHAPA PEPVADVCSD SDNDGVCDNV DKCPDTPANV TVDANGCPAV AEVVRVQLDV
 61 KFDFDKSKVK ENSYADIKNL ADFMKQYPST STTVEGHTDS VGTDAYNQKL SERRANAVRD
121 VLVNEYGVEG GRVNAVGYGE SRPVADNATA EGRAINRRVE SSHSKETEAR LTATEDAAAR
181 AQARADEAYR KADEALGAAQ KAQQTADEAN ERALRMLEKA SRK SEQ ID NO: 10 (OprF/I with Cys18-Cys27-bond and a Cys33-Cys47-bond)
Disulfide bond between Cys18-Cys27 (both underlined) and Cys33-Cys47 (both italic)
  1 AHHHHHHAPA PEPVADVCSD SDNDGVCDNV DKCPDTPANV TVDANGCPAV AEVVRVQLDV
 61 KFDFDKSKVK ENSYADIKNL ADFMKQYPST STTVEGHTDS VGTDAYNQKL SERRANAVRD
121 VLVNEYGVEG GRVNAVGYGE SRPVADNATA EGRAINRRVE SSHSKETEAR LTATEDAAAR
181 AQARADEAYR KADEALGAAQ KAQQTADEAN ERALRMLEKA SRK SEQ ID NO: 11 (OprF/I with Cys18-Cys47-bond and a Cys27-Cys33-bond)
Disulfide bond between Cys18-Cys47 (both underlined) and Cys27-Cys33 (both italic)

-continued

SEQUENCES

```
  1 AHHHHHHAPA PEPVADVCSD SDNDGVCDNV DKCPDTPANV TVDANGCPAV AEVVRVQLDV

61 KFDFDKSKVK ENSYADIKNL ADFMKQYPST STTVEGHTDS VGTDAYNQKL SERRANAVRD

121 VLVNEYGVEG GRVNAVGYGE SRPVADNATA EGRAINRRVE SSHSKETEAR LTATEDAAAR

181 AQARADEAYR KADEALGAAQ KAQQTADEAN ERALRMLEKA SRK

SEQ ID NO: 12 (spacer)
  1 STGS
```

EXPERIMENTAL PART OF THE INVENTION

Abbreviations

| Abbreviation | Explanation |
| --- | --- |
| AUC | Analytical ultracentrifugation |
| CV | Column volume |
| DTT | Dithiothreitol |
| DV | Diafiltration volumes |
| DS | Drug substance |
| ED50 | Reverse of the dilution of the samples resulting in 50% seroconversion rate |
| EGT | Eurogentec |
| gDNA | Genomic DNA |
| GMT | Geometric mean titer |
| GSH | Reduced glutathione |
| GSSG | Oxidized glutathione |
| HCP | Host cell protein |
| HPLC | High performance liquid chromatography |
| ICLL | Intercell |
| IMAC | Immobilized metal affinity chelate chromatography |
| MALDI-ToF | Matrix assisted Lased Desorption Ionization Mass Spectrometry-Time of Flight |
| MALS | Multi Angle Light Scattering |
| β-ME | Beta-mercaptoethanol |
| PAGE | Polyacrylamide gel Electrophoresis |
| QSHP | Q-Sepharose HP |
| RP | Reversed phase |
| RT | Room temperature (about 20° C.) |
| SCD | Sedimentation Coefficient Distributions |
| SEC | Size exclusion chromatography |
| UF/DF | Ultrafiltration/Diafiltration |

Materials

NaOH (Riedel-de Haen), NaCl (Riedel-de Haen), Tris(hydroxymethyl)aminomethane (Merck KGaA, Darmstadt), L-Cystine (Aldrich), DTT (Sigma), HCl (Merck KGaA), Q-Sepharose® HP (GE Healthcare), DEAE-Sepharose® FF (GE Healthcare). All other materials were of analytical grade if not otherwise stated.

Formulation buffer: Dulbecco's 1×PBS pH 7.4 (H15-002), 1× concentrate (g/L)

| | |
| --- | --- |
| KCl | 0.2 g/L |
| KH$_2$PO$_4$ | 0.2 g/L |
| NaCl | 8.0 g/L |
| Na$_2$HPO$_4$ anhydrous | 1.15 g/L |

General Methods
Analytical RP-HPLC

Analytical RP-HPLC analysis of samples was performed on a Jupiter C4 column (4.6 mm×150 mm, 300 A, 5 μm, Phenomenex) connected to a Dionex Ultimate 3000 HPLC system. Solvent A was water containing 0.1% TFA, solvent B was acetonitrile containing 0.1% TFA. Separation of peaks was performed by linear gradient elution from 27% B to 37% B in 13 min at a flow rate of 1 mL/min. The column temperature was set to 40° C. Peak detection was performed at 214 nm and 280 nm.

For downstream development work an estimation of the specific OprF/I content in IMAC/G50 was necessary to calculate step yields. OprF/I content was determined by RP-HPLC. The HPLC system was calibrated with purified, native (unreduced) OprF/I working standard. The protein content of the working standard was determined by UV 280 nm measurement based on a calculated theoretical extinction coefficient for a 1 mg/mL solution of $\epsilon_{0.1\%}$=0.373. Prior to analysis of IMAC/G50 pools by RP-HPLC, an aliquot was fully reduced by addition of DTT or β-mercaptoethanol (100 mM final concentration) to split up the various aggregated and misfolded (most probably disulfide scrambled) OprF/I variants. The samples were incubated at room temperature for 30 minutes and analyzed by RP-HPLC. After reduction, OprF/I eluted as a single peak compared to the untreated IMAC/G50 pool. The content of reduced OprF/I after IMAC/G50 was calculated by integration of the peak area.

All other samples (e.g. reoxidized OprF/I, fractions from QS-HP etc.) were directly injected without further treatment and the OprF/I concentration was calculated.

Reoxidized samples can be immediately analyzed by RP-HPLC or formation of disulfide bonds can be quenched by acidification to pH 2-3 (~20 μL 6% HCl per 1 ml reoxidation solution) and stored at 2-8° C. for subsequent analysis.
Semi-Preparative RP-HPLC Semi-Preparative RP-HPLC was used for isolation of individual peaks detected by analytical RP-HPLC. Purification was done on a Jupiter C4 column (10 mm×250 mm, 300 A, 5 μm, Phenomenex) connected to an Äkta Purifier chromatography system. The stationary phase at preparative scale was the same as the one used at analytical scale. Solvent A was water containing 0.1% TFA, solvent B was 80% acetonitrile in water containing 0.1% TFA. Sample volume was 2 to 4 mL (total protein load <2 mg). Separation of peaks was performed by linear gradient elution from 35% B to 40% B over 8 column volumes at a flow rate of 2.5 mL/min. The column temperature was set to 40° C. Peak detection was done at 280 and 214 nm Fractions of 0.8 mL were collected and the pH was adjusted to pH ~7 by addition of 0.25 mL 0.1 M sodium phosphate buffer, pH 7.0. Higher quantities (~0.5 to 2 mg) of P1 to 4 were prepared by several preparative purification runs. After pooling of the desired fractions containing the individual peaks, samples were concentrated approximately 5 times using a 5 kDa ultracentrifugation device (Millipore). Concentrated pools were desalted by PD10 columns (GE Healthcare) and the buffer was exchanged against final drug product formulation buffer (1/10 PBS diluted with 0.9% NaCl, pH ~7). Final samples containing the isolated OprF/I variants were analyzed for purity and content by RP-HPLC and SEC-HPLC. The relative purity determined by RP-HPLC was at least 90%. Samples were stored at −20° C. until further analysis.

SDS-PAGE

SDS-PAGE was done on 4-12% NuPAGE gels (Invitrogen) using MES running buffer. Samples were mixed with LDS sampling buffer under reducing or non-reducing conditions and incubated for 5 min at 70° C. if not otherwise stated Staining was done with colloidal Commassie or silver stain (Heukeshoven).

Western Blot Analysis

Western blotting was done with antibodies anti OprF/I 944/5 D5 epitope (1:20000 diluted) and 966/363 E3 epitope (1:10000 diluted).

pH and Conductivity Measurement

For determination of pH and conductivity of samples and buffers a WTW 720 system was used. Conductivity was measured using the linear temperature compensation mode at 25° C.

Endotoxin Measurement

Endotoxin measurement was done with a chromogenic LAL-assay (Cambrex). Selected samples were also measured in an external certified laboratory with a conventional gel clot assay (Limulus Amoebocyte Lysate test).

Host Cell Protein Measurement (HCP)

For quantification of HCPs, a generic *E. coli* HCP ELISA kit (Cygnus Technologies, Inc.) was used.

Peptide-Mass Fingerprint and Disulphide Mapping

Purified fractions obtained from preparative RPC were analyzed by LC-MS/MS. Samples were digested with AspN or trypsin without reduction or after reduction and alkylation.

MALDI-ToF Mass Spectrometry

MALDI-ToF analysis was performed on a Voyager STR 4069 system (Applied Biosystems). Sinapinic acid dissolved in 0.1% TFA/30% AcN was used as sample matrix. DS samples were diluted five-fold with sample matrix and 2 µl were placed on the target. A delayed extraction mode and positive polarity was used. The system was externally calibrated with BSA (Mass calibration kit, Applied Biosystems). For internal calibration Myoglobin (Sigma M-0630, average Mr 16951.5) was spiked into DS samples at a concentration of approximately 100 µg/mL. The mass accuracy for internal calibration can be estimated with approximately ±0.3% (e.g. 24100±72 Da), for external calibration ±0.6% (e.g. 24100±145 Da).

Native PAGE

The NativePAGE™ Novex® Bis-Tris Gel system is a near neutral pH, pre-cast polyacrylamide mini gel system to perform native (non-denaturing) electrophoresis. Native PAGE of OprF/I fusion protein samples was done on NativePAGE 4-16% Bis-Tris gels (Invitrogen) according to the manufacturers instruction. Sample buffer was 50 mM BisTris, 50 mM NaCl, 16 mM HCl, 10% w/v Glycerol, 0.001% Ponceau S, pH 7.2. Running buffer was 50 mM BisTris, 50 mM Tricine, pH 6.8. Cathode buffer was running buffer including 0.02% Coomassie G-250.

N-terminal Sequencing

N-terminal sequencing was carried out using an Applied Biosystems 494HT machine and the method of N-terminal Edman sequencing, where the N-terminal amino acid of the protein was sequentially removed chemically and identified by HPLC. The protein was first immobilized inside the sequencing instrument by either blotting it onto a PVDF membrane or adsorbing it onto a biobrene treated glass fibre filter. Subsequently the bound protein reacted with the Edman reagent, (phenylisothiocyanate, PITC) at high pH. After this reaction, the resulting compound was cleaved off the protein using anhydrous acid. The coupling and cleavage process was repeated for as many times as required. Usually 15 to 20 amino acids ("amino acids" herein also referred to as "aa") could be analyzed. The cleaved products were converted to their stable phenylthiohydantoins, PTH, with aqueous acid, and then analyzed using the on-board HPLC. Identification of the amino acids was achieved by comparing elution times compared to a standard mixture. Data from the HPLC was collected on a computer for visual calling of the sequence.

Alkylation of Thiolgroups

Free thiol groups in proteins can be detected by alkylation using iodoacetamide, which reacts selectively with free thiol groups of cysteines to produce carboxamidomethyl cysteine. If free thiol groups are present, these would be covalently blocked resulting in a mass increase of 57 Da per attached iodacetamide molecule.

47 mg iodoacetamide were dissolved in 1 mL 1 M Tris-HCl, pH 8.0 (0.2 M iodoacetamide solution). 200 µL each of purified peak 1, 2 and 3 (protein concentration approximately 200 µg/mL) were mixed with 20 µL of iodoacetamide stock solution (final iodoacetamide concentration ~0.02M). The OprF/I fusion protein sample (protein concentration approximately 1 mg/mL) was 3 fold diluted with PBS to a final concentration of approximately 330 µg/mL. 30 µL iodoacetamide stock solution were added to 300 µL diluted DS. In another experiment the sample was reduced with 5 mM DTT (20 min) before dilution and alkylation. All samples were incubated at room temperature in the dark for 30 min followed by LC-MS analysis.

Static Light Scattering Analysis

The chromatographic system consisted of an HPLC system from Dionex including an Ultimate 3000 pump and degasser, an Ultimate 3000 autosampler and an Ultimate 3000 column compartment. Column and chromatographic conditions were the same as described for SEC-HPLC. All solvents were filtered through a 0.1 µm Supor Membrane filter (Pall Vacu-Cap 60). An injection volume of 100 µL was used for all samples if not stated otherwise.

Chromatographic detectors included a Dionex Ultimate 3000 photodiode array detector set to 214 nm and 280 nm, a Shodex RI-101 refractive index detector and a DAWN TREOS MALS (multi angle light scattering) detector (Wyatt Technology Corporation), which was used in on-line mode. Chromatographic data collection and analysis was performed using the Chromeleon software package (vers. 6.80, Dionex). Experimental collection and data analysis of the MALS-signals were performed with the ASTRA software package (version 5.3.2.13, Wyatt Technology). Using this software it was possible to collect and subsequently analyze the light scattering signals (3 MALS angles) along with the UV-, and RI-signals.

Analytical Ultracentrifugation (AUC)

All experiments were performed with a BeckmanCoulter XL-I Analytical Ultracentrifuge at 50,000 rpm and 25° C. Samples were placed in sapphire-capped two-sector titanium centerpieces of 12 mm optical path length. 390 µL of solution and solvent were placed in the sample and reference sectors, respectively. Sedimentation traces were detected by recording local differences in refractive index (interference optics). The samples were analyzed with a ten-fold dilution or without further dilution. Diffusion-corrected Sedimentation Coefficient Distributions (SCD) were calculated using the finite element approach proposed by P. Schuck, NIH (Peter Schuck et al., Biopolymers, Vol 54, Issue 5, pages 328-341, October 2000). The frictional ratio f/f0 was treated as a fitting variable. The density and viscosity of the buffer (phosphate buffered saline, PBS) as well as the partial specific volume (v)

of the proteins were calculated from composition with Sednterp. These values were used when calculating the respective SCD.

Analysis of OprF/I Fusion Protein Samples Including Aluminium Hydroxide by RP-HPLC Aliquots (0.25 ml) of formulated OprF/I fusion protein were centrifuged at 16000×g for 10 minutes at 20° C. to separate the aluminium hydroxide sediment from the supernatant. The clear supernatant was removed and used for analysis of unbound fusion protein by RP-HPLC. The remaining pellet was resuspended in 0.25 ml of 0.1% TFA in water (pH ~2). Samples were incubated at RT for 2 h, followed by 10 minutes centrifugation at 16,000 g at room temperature to spin down the Aluminium particles. The clear supernatant was used for analysis by RP-HPLC (TFA desorption).

Specific Methods and Results

Expression and Recovery of OprF/I Fusion Protein

OprF/I is a fusion protein of the pseudomonas outer membrane porin proteins OprF and OprI. It is expressed as a 224 aa hybrid protein containing a $His_6$-tag at its N-terminus. The N-terminal Met is cleaved off after expression in E. coli. The primary structure of the expressed protein (including the N-terminal methionine) is shown in SEQ ID NO: 3.

The molecular weight of the native protein has been calculated as 24118.2 Da (full reduced protein, no N-terminal methionine). The pI has been calculated as 5.3.

The protein of the present examples is a fusion protein of outer membrane protein F and I containing a N-terminal histidine tag (His tag). The protein was expressed in E. coli XL1-Blue/pTrc-Kan-OprF/I-His strain. The OprF/I-His protein was expressed intracellularly in soluble form at 30° C.

Cell Lysis

OprF/I may be degraded by bacterial proteases, in particular when lysis buffer without high concentration of NaCl and imidazole was used. Therefore, cells were resuspended in cold lysis buffer (1:5 dilution of cell paste in buffer) consisting of 0.1 M Tris, pH 7.4, 0.5 M NaCl, 0.06 M imidazole. Addition of 0.5 M NaCl particularly inhibited proteolytic degradation of the molecule in the lysate. Resuspension and subsequent homogenization (2 cycles at 800 bar) was done at cold room temperature and the lysate was placed on ice immediately. Higher temperatures may lead to product degradation or higher protease activity.

IMAC-Copper Capture Step

Chelating Sepharose FF (loaded with copper ions) was used for capturing the His-tagged OprF/I. After loading the lysate, elution was performed with different concentrations of imidazole: 0.07 M, 0.325 M and 0.5 M imidazole. OprF/I containing fractions elute at 0.325 M imidazole as two separate peaks. Analytical data showed that RP-HPLC elution profile contained several peaks. If the same samples were analyzed under reduced conditions (addition of DTT or β-ME) only one major peak was observed. The various peaks in the untreated sample were most probably disulfide scrambled variants and aggregates of the native molecule.

An exemplary purification run was done with 992 g cell paste that is equivalent to 8.59 L of fermentation broth. After the IMAC purification and desalting on Sephadex® G50 (see below) the total amount of OprF/I was approximately 1600 mg which is equivalent to 186 mg OprF/I per liter fermentation broth.

Desalting on Sephadex G50

This step reduced the content of low molecular weight impurities (e.g. imidazole, copper, etc.) and a buffer exchange was conducted. The loading volume was approximately 20% of the column volume. As elution buffer 0.1M Tris-HCl, 0.15M NaCl, pH 8.0 was used. It was the same buffer used for reduction and reoxidation. Alternatively, this step was also replaced by UF/DF with a 100K cut-off membrane.

Reduction

After the IMAC/G50 steps, OprF/I exists as heterogeneous mixture of misfolded forms (high and low molecular weight aggregates) caused by disulfide scrambling as schematically depicted in FIG. 1. Reduction of disulfide bonds was done with 5 mM DTT to break up all intra- and intermolecular disulfide bonds. The fully reduced protein elutes as a single peak according to RP-HPLC data. DTT can be substituted by β-ME. Since DTT is not stable over a longer period of time in aqueous solution, an aliquot of a freshly prepared DTT solution (1 M in water, used within 1 hour) is added to the IMAC/G50 pool under gentle stirring (5 mL of 1 M DTT stock solution per liter IMAC/G50 pool). The pool is incubated at room temperature for 30 minutes without stirring. Samples can be analyzed by RP-HPLC to monitor the progress of reduction.

Reoxidation

For optimization of the reoxidation conditions, different redox systems (GSSG/GSH, cystamine/cysteamine, cystine/cysteine) were tested out in presence of low concentration of DTT (1 mM) to allow correct reshuffling of the disulfide bond. The progress of reoxidation (formation of disulfide bonds) can be monitored by RP-HPLC after various time intervals since the folding variants have different retention times. Reoxidation with cystamine/cysteamine was unsuccessful under the tested conditions. In a first set of experiments, GSSG and GSH were tested out as reoxidation agents. The reduced IMAC/G50 pool in 5 mM DTT was diluted 5-fold into 0.1 M Tris-HCl, 0.15 M NaCl pH 8.0 containing GSSG (0-4 mM) under gentle stirring. DTT reacts with GSSG and forms GSH, GSSG and reduced/oxidized DTT. The final reoxidation conditions tested out covered a broad range of different ratios of GSH, GSSG and DTT. Aliquots of the samples were also quenched with HCl after various time intervals and analyzed by RP-HPLC. At increasing GSSG concentration peak 1 increases and peak 2 decreases. Formation of peak 1 occurs very early in the reoxidation process and remains constant over time. The total recovery for peaks 1+2 was estimated to be ~60% starting from the completely reduced protein (100%), the recovery of all detected peaks was approximately 90% compared to the starting material.

In a second set of experiments, cystine and cysteine were tested out as reoxidation agents. The reduced IMAC/G50 pool (5 mM DTT) was diluted 5-fold into 0.1 M Tris-HCl, 0.15 M NaCl pH 8.0 containing various concentration of cystine (0-3 mM) and cysteine (0-3 mM). The final DTT concentration was 1 mM. Please note that the 0.2 M stock solution of cystine was prepared in 0.5 M NaOH. Samples were analyzed after 300 min and over night incubation at room temperature. No difference in RP-HPLC peak pattern for each individual experiment between the two time points was observed except for the sample containing 1 mM DTT and no cystine. The protein was still reduced after 5 h, after over night incubation peak 2 appeared. Depending on the final cystine and cysteine concentration, different ratios of peak 1 and peak 2 were detected. RP-HPLC profiles showed that peak 1 concentration was sufficiently low in presence of 0.5 mM cystine.

Figure 2:
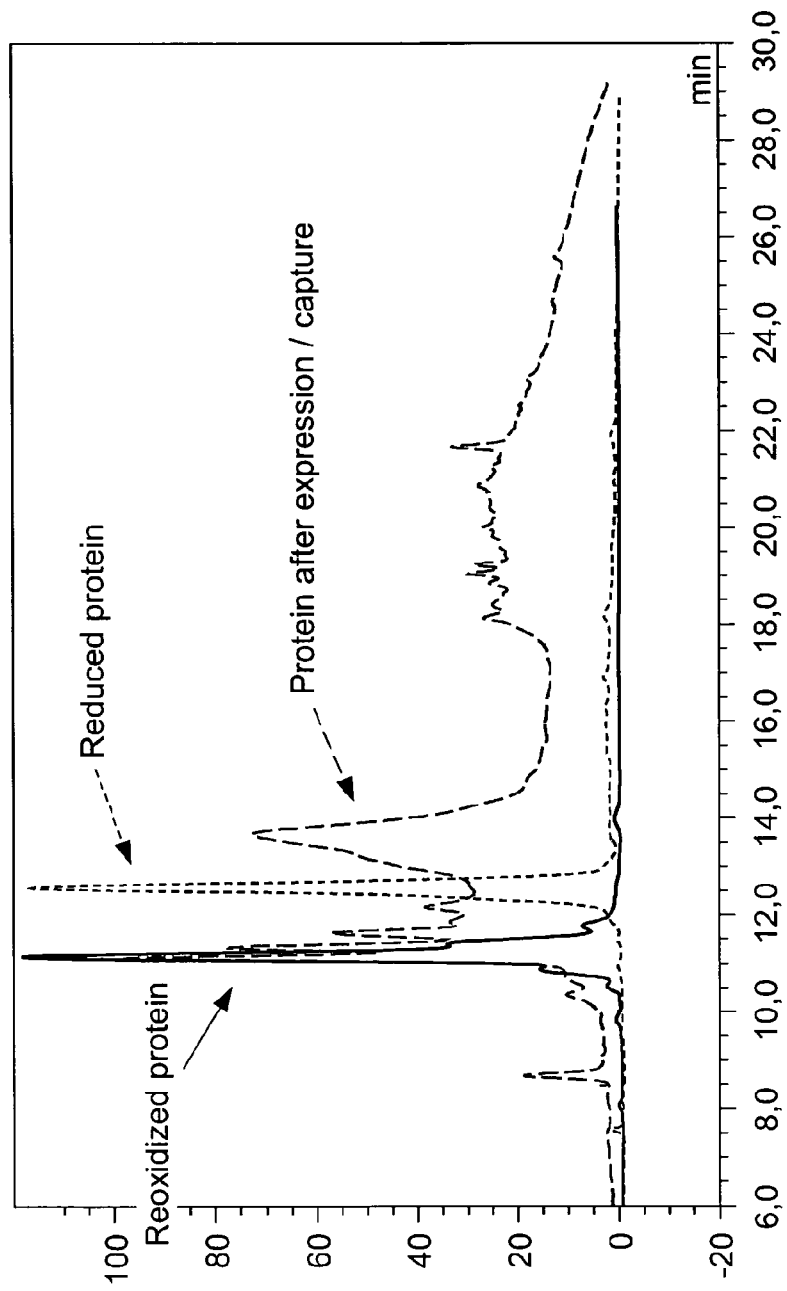
FIG. 2 shows the superimposition of RP-HPLC profiles of the OprF/I fusion protein after expression and capturing on IMAC, after reduction, and after reoxidation/purification.
Figure 3:
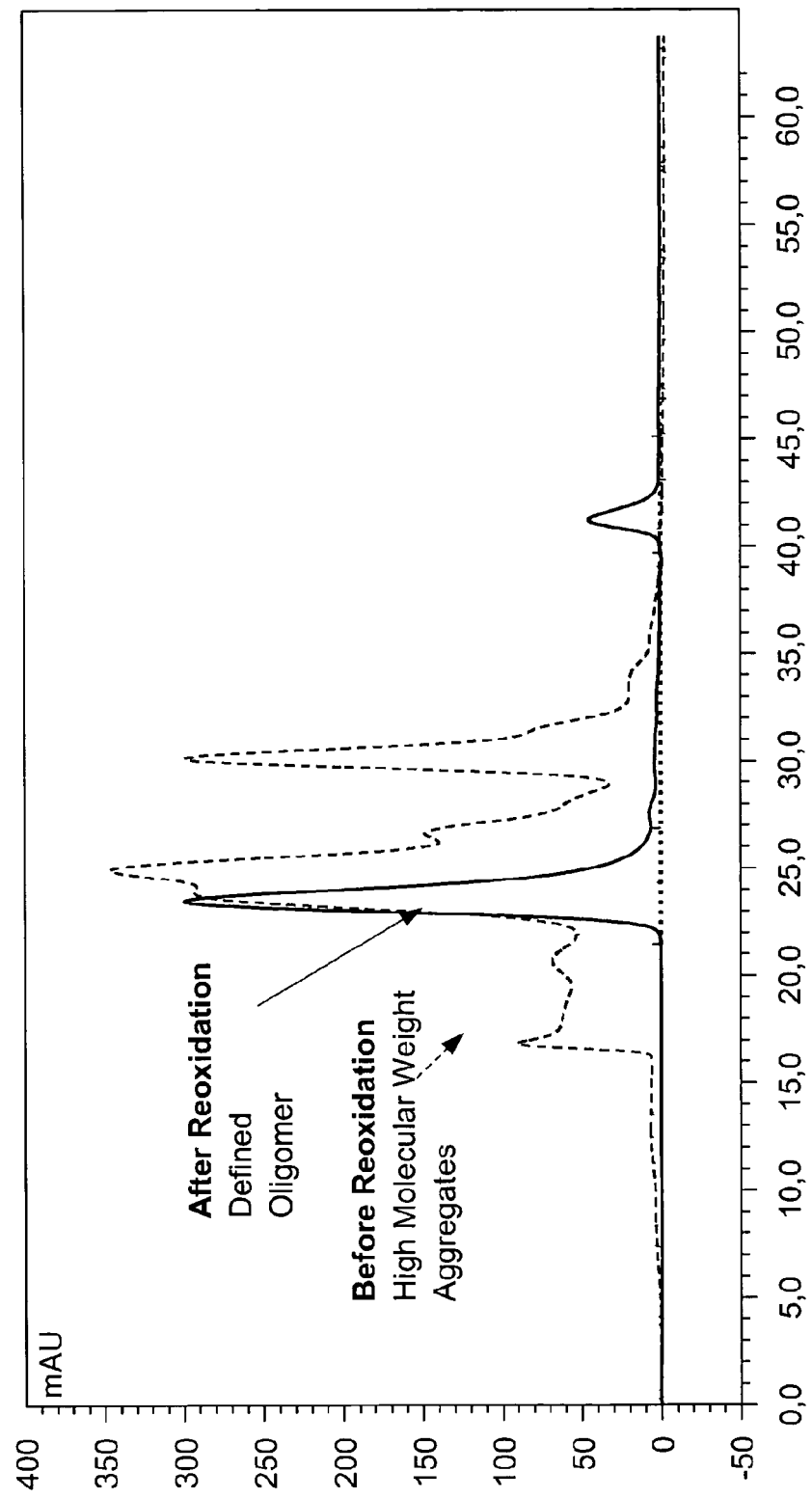
FIG. 3 shows the superimposition of SEC profiles of the OprF/I fusion protein after expression and capturing on IMAC, and after reoxidation/purification.
Figure 4:
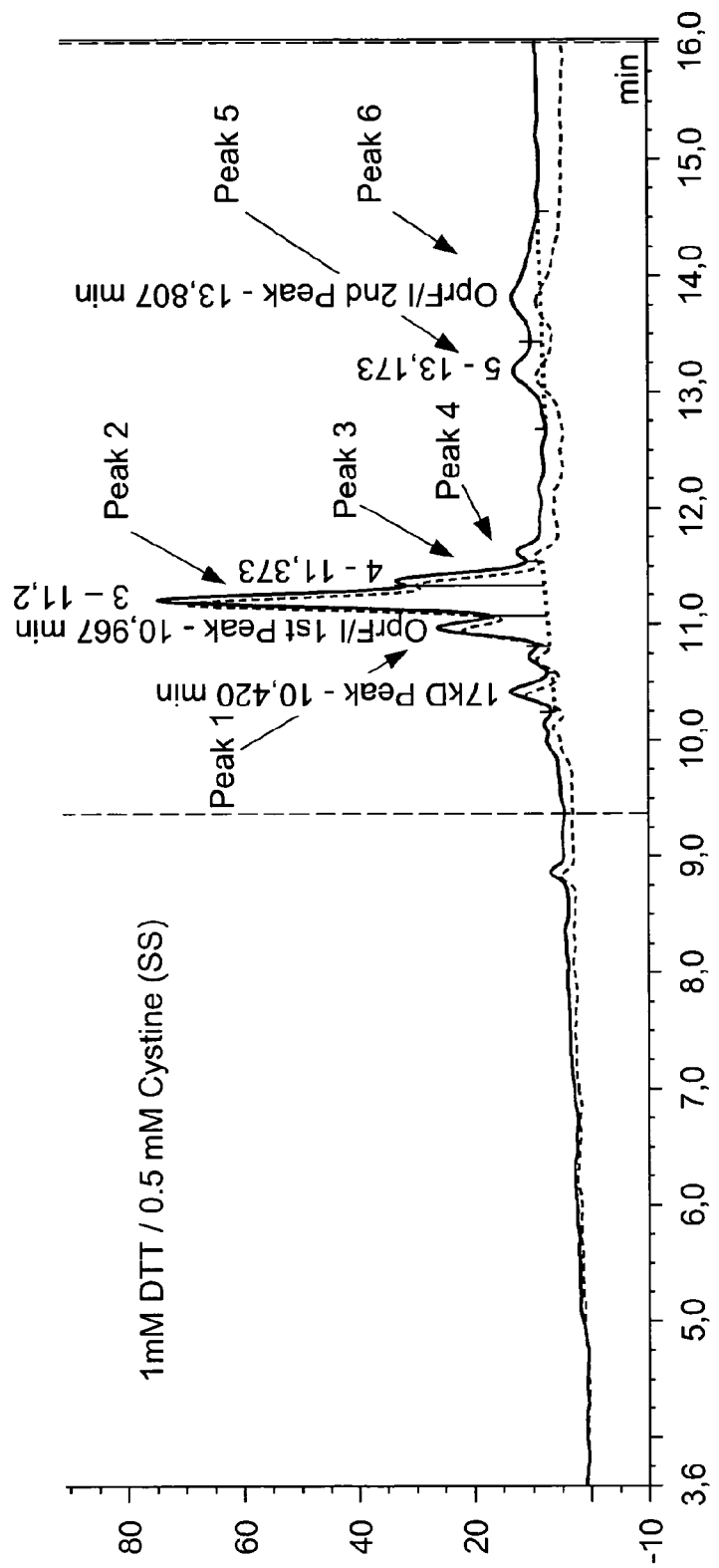
FIG. 4 shows the RP-HPLC analysis of the reoxidized IMAC/G50 pool. Samples were analyzed after 300 minutes and 21 hours.

After preliminary studies of the various redox systems, it was decided to use cystine as the oxidizing agent. During scale-up of the production process for GMP production the concentration was further lowered to 0.375 mM cystine. Representative RP-HPLC and SEC elution profiles prior and after reduction/reoxidation of IMAC/G50 pool are shown in FIG. 2 and FIG. 3. After reoxidation in presence of 0.5 mM cystine, the elution profiles observed by RP-HPLC and SEC were much more homogeneous compared to the "untreated" IMAC/G50 pool. The various peaks, present in the IMAC pool before reduction, shift to one major peak under reducing conditions. After reoxidation, one major peak (named as peak 2 in FIG. 4) is observed with a different retention time compared to the reduced protein. Peak 2 should represent the correctly folded OprF/I. Peak 2 is surrounded by three smaller peaks (peak 1, peak 3 and peak 4 in FIG. 4) that should be folding variants. Peaks eluting at approximately 13.17 and 13.81 min, named as peak 5 and peak 6 in FIG. 4, are other folding variants (disulfide cross-linked aggregates according to MS data).

Further characterization of peak 1 by LC-MS showed an increase in molecular weight of 240 Da compared to peak 2. This mass shift was most probably caused by covalent attachment of two molecules cysteine. Free cysteine was formed by the reaction of DTT with cystine, which resulted in 2 molecules cysteine. It was further discovered that peak 1 increases while peak 2 decreases at increasing concentration of oxidizing agent (GSSG or cystine).

Figure 5:
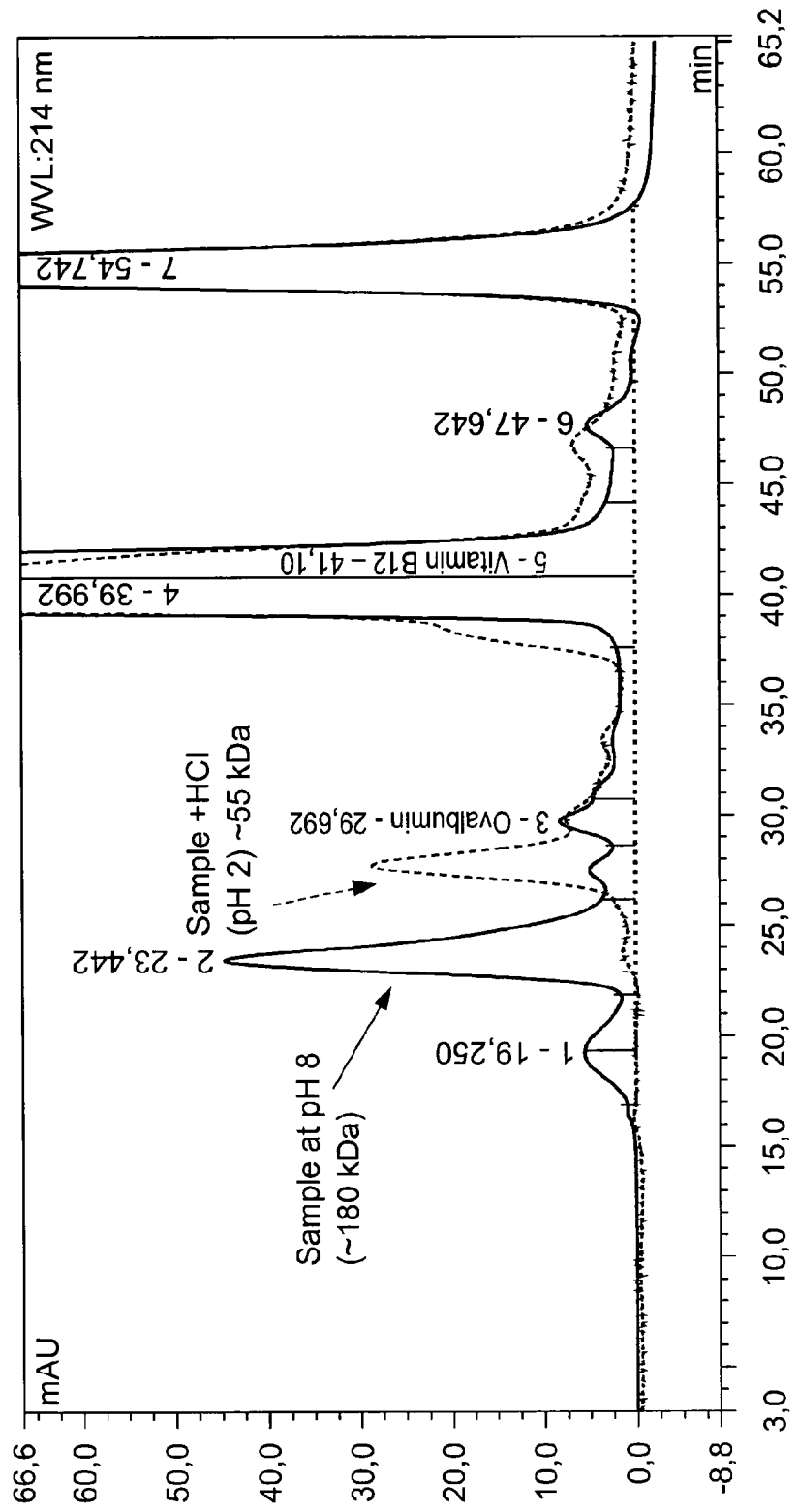
FIG. 5 shows the change in retention time during SEC analysis of OprF/I fusion protein samples at pH 8.0 and pH 2.

Evaluation of the main peak after reoxidation by SEC shows that the protein does not exist as a monomer. The SEC column was calibrated with reference proteins (BioRad's size exclusion standard) ranging from 1.35 to 670 kDa. The retention time of the main peak (~25 min) corresponds to a calculated theoretical mass of ~180 kDa under the assumption of a globular shape and no unspecific interactions with the stationary phase. It was observed that this defined multimeric state was formed preferential under the process and formulation conditions applied and seemed to be stable in aqueous solution at neutral pH in presence of NaCl. At pH 7 to 8 the OprF/I fusion protein elutes as a multimer corresponding to 180 kDa, whereas in the acidified sample (pH ~2) the peak shifts to higher retention time (~28 min) corresponding to approximately 55 kDa (see FIG. 5). This change in retention time could be caused by dissociation of the multimer at low pH.

Purification by DEAE Sepharose FF

Additional purification of the OprF/I containing process stream by anion exchange chromatography after reoxidation was tested out to reduce the content of remaining endotoxins and gDNA. These remaining impurities would bind to anion exchange media at neutral to slightly basic pH even at higher conductivity, whereas the product should remain in the flow through. DEAE Sepharose was tested out and found to have good properties to remove endotoxins without any major product losses by binding of OprF/I onto the resin.

Purification by Q-Sepharose HP (QSHP)

After reoxidation and DEAE flow through chromatography, the protein solution was further purified by Q-Sepharose HP. Purification by QSHP resulted in an endotoxin concentration of ~2 EU/mg in the main pool, which was within an acceptable low level.

Ultrafiltration/Diafiltration

Finally, the QS-HP pool was diafiltrated against formulation buffer (1×PBS buffer pH 7.4, Dulbecco, without Ca, Mg). A 10 kDa or 30 kDa regenerated cellulose membrane (Amicon Ultra 15 centrifugal filter device, Millipore), was used. OprF/I was detected in the permeate of the 30 kDa membrane. Therefore, a 10 kDa membrane was used for final UF/DF into formulation buffer resulting in a step yield of >95%. The pool was adjusted to a final protein concentration of 1 mg/ml based on UV measurement.

Figure 6:
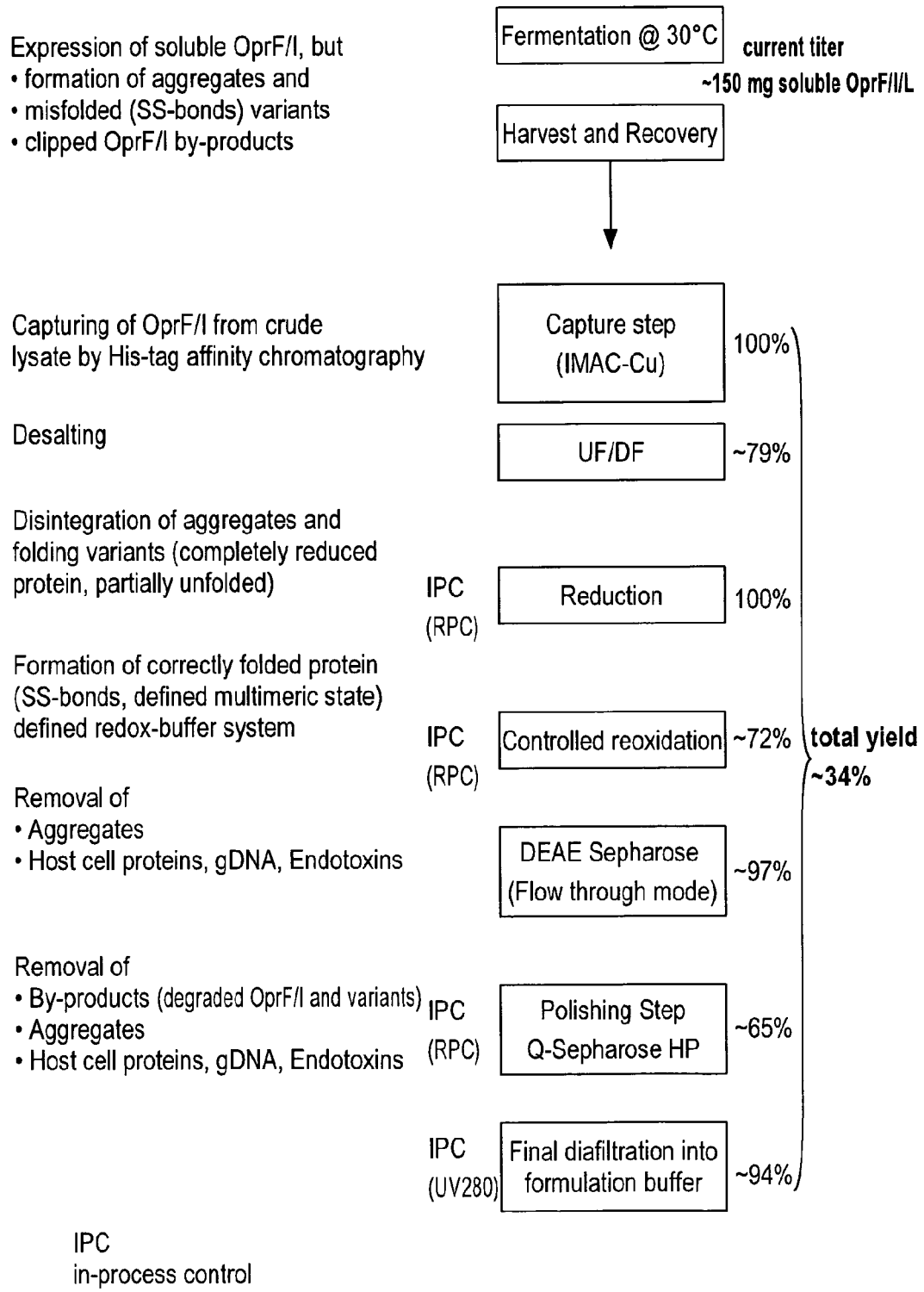
FIG. 6 shows a flow scheme of an exemplary production and purification process of the OprF/I fusion protein.

An overview of the whole production and purification process is shown in FIG. 6. An overall yield of about 34% to about 40% of purified OprF/I fusion protein was achieved.

Figure 7A:
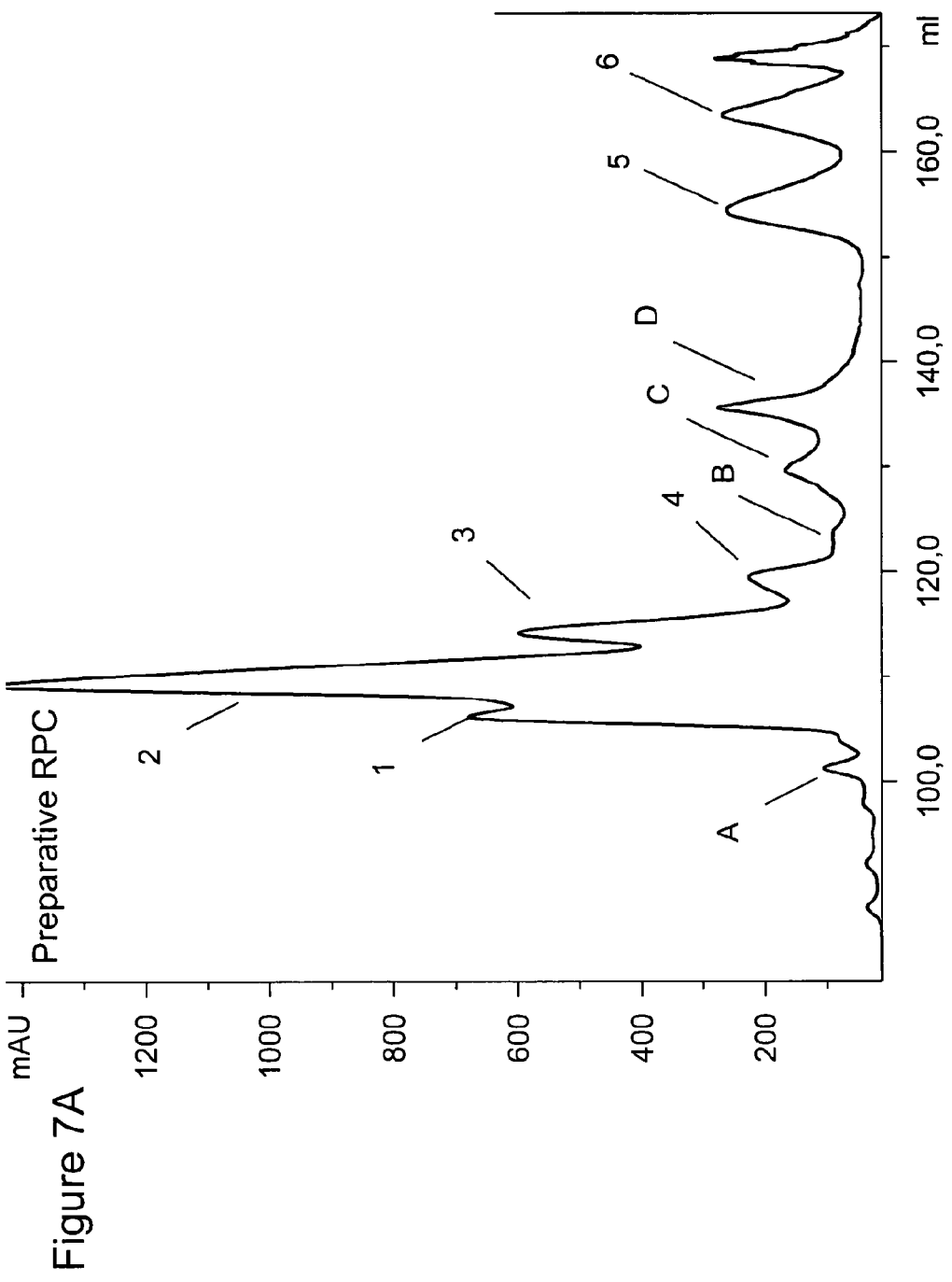
FIG. 7A shows preparative RP-HPLC elution profiles.
Figure 7B:
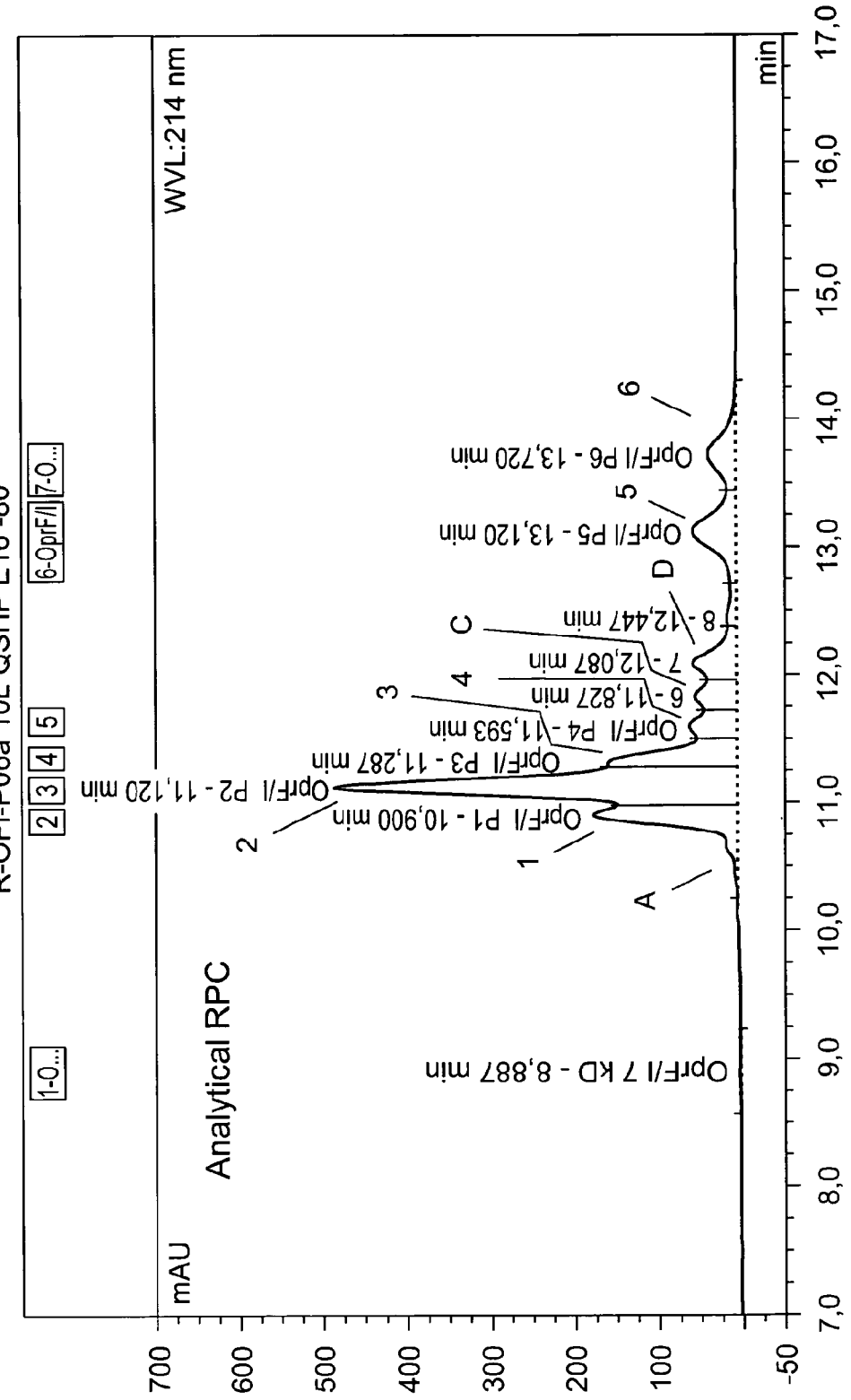
FIG. 7B shows analytical RP-HPLC elution profiles of an elected QSHP fraction.

Characterization of the Purified OprF/I Fusion Protein
Preparative Isolation of OprF/I Fusion Protein Variants Selected side fractions from QSHP chromatography steps were used for preparative isolation. A typical preparative elution profile and nomination of peaks detected is shown in FIGS. 7A and 7B. All combined fractions containing the individual peaks were analyzed by SDS-PAGE and Western blot under reducing and non-reducing conditions. Under reducing conditions all bands had similar migration properties compared to an OprF/I standard. Under non-reducing conditions, the content of multimeric OprF/I variants detected at approximately 60 kDa (calibrated against the molecular weight marker) increased for Peak C, D, 5 and 6. All bands were also detected by western blot analysis using monoclonal anti OprF/I antibodies. These results indicate that all peaks detected by RP-HPLC are product related. This finding was also confirmed by peptide-mass fingerprint analysis of the individual fractions. In final DS only P1, 2, 3, 4 and 5 can be detected by RPC. The other peaks, A, B, C, D and 6, could be separated by preparative chromatography on Q-Sepharose HP from the main fractions. During Q-Sepharose HP chromatography a small peak eluted before the main peak. This fraction contained a higher concentration of an OprF/I degradation product (denoted as 7 kDa peak) as detected by analytical RP-HPLC and MALDI-ToF. This peak was also shown to be a product related fragment consisting of a 15.5 kDa and 7.2 kDa OprF/I fragment.

Analytical Characterization of OprF/I Fusion Protein Variants

The purified OprF/I fusion protein consists of different forms of the molecule as shown by RP-HPLC (see FIG. 4). Five peaks could be detected by RP-HPLC. Peak 2 (P2) was the most prominent peak with a relative content of 50 to 55%, surrounded by peak 1 (P1), peak 3 (P3) and Peak 4 (P4). Peak 5 (P5) was well separated from the other peaks eluting at a slightly higher retention time. The relative peak content is summarized in Table 1. After reduction of the sample with β-ME or DTT, the elution profile changes. One major peak eluted and the individual variants exhibited the same chromatographic retention time. Based on these results P1 to P4 are regarded as folding variants caused by differences in disulphide bonding.

TABLE 1

| Peak | Sample 1 | Sample 2 | Sample 3 | Sample 4 |
| --- | --- | --- | --- | --- |
| 1 | 19% | 14% | 13% | 11% |
| 2 | 50% | 55% | 54% | 60% |
| 3 | 18% | 17% | 19% | 14% |
| 4 | 9% | 9% | 9% | 9% |
| Sum of Peaks 1, 2 and 3 | 87% | 86% | 86% | 85% |

Note:
Reoxidation of sample 1 was done in presence of 0.5 mM cystine; samples 2, 3 and 4 were reoxidized in presence of 0.375 mM cystine. The slightly higher cystine concentration resulted in minor increase in peak 1 content for sample 1.

MALDI-ToF Analysis

For MALDI-ToF analysis the system was calibrated externally against BSA. For internal calibration Myoglobin was used. All four samples showed similar mass spectra. The main signal was from native OprF/I monomer followed by OprF/I dimer and trimer peaks. Table 2 summarizes molecular mass obtained after internal calibration. Deviation from the expected molecular mass was within the experimental error (±0.3%). Mass peaks at 24 kDa, 48 kDa and 72 kDa were detected, showing the presence of the monomeric, dimeric and trimeric OprF/I fusion proteins.

TABLE 2

| Peak | Analyzed mass (Da) | Deviation from theoretical mass (Da)* (rel. % deviation from theoretical MW) |
|---|---|---|
| Monomer | | |
| Sample 1 | 24096 | −20 (−0.08) |
| Sample 2 | 24053 | −63 (−0.26) |
| Sample 3 | 24097 | −19 (−0.08) |
| Sample 4 | 24045 | −71 (−0.30) |
| Dimer | | |
| Sample 1 | 48408 | +176 (+0.36) |
| Sample 2 | 48104 | −128 (−0.27) |
| Sample 3 | 48239 | −7 (−0.01) |
| Sample 4 | 48031 | −201 (−0.42) |
| Trimer | | |
| Sample 1 | 72379 | +31 (+0.04) |
| Sample 2 | 72105 | −243 (−0.34) |
| Sample 3 | 72135 | −213 (−0.30) |
| Sample 4 | 72250 | −98 (−0.14) |

*theoretical mass: monomer 24114 Da under the assumption of two disulfide bonds, dimer 48228, trimer 72342

Native PAGE

Native PAGE of OprF/I fusion protein samples under non-reducing and reducing conditions were carried out as explained above. Band intensities after Commassie blue staining were evaluated by densitometry. Under native conditions one OprF/I main band was detected in the range of approximately 180 kDa with a relative intensity of approximately 94 to 97%. Under reducing conditions the apparent molecular size was determined as 206 kDa. The apparent molecular weight is in good correlation with SEC-HPLC data, but different from SEC-MALS and AUC results where OprF/I mass was in the range of 80 kDa (trimer). The separation mechanism for native PAGE is the same as for native SEC, separation properties strongly depend on the shape of the protein complex when it passes through the gel. This result confirms that OprF/I has a rather elongated shape with a high hydrodynamic radius.

N-terminal Sequencing

The first 13 or 15 amino acids of two different samples were analyzed. No differences between the theoretical and detected amino acid sequence were found. The sequencing results confirmed that the N-terminal Met was completely cleaved off during expression.

Alkylation of Thiolgroups

The results of the alkylation of the thiogroups of a OprF/I fusion protein sample showed a mass increase after alkylation of +226 Da corresponding to 4 attached molecules of iodacetamide (theoretical mass increase +228 Da; mass increase of +57 Da per attached iodacetamide molecule). This result was expected since the reduced protein contains 4 free cysteine residues. All other samples did not show an increase in mass. Based on these results peak P1 of the RP-HPLC (FIG. 4) could be considered as a twofold cysteinylated variant containing one additional disulphide bond. Peaks P2 and P3 were considered as variants containing two disulphide bonds.

Static Light Scattering (SEC/MALS)

SEC with refractive index/UV detection at 280 nm was combined with light scattering for protein characterization and molecular weight detection. As the molar mass was constant over the cross section of the main peak eluting between 23 to 26 min, a defined monodisperse molecule species eluted. For the main peak a molecular mass in the range of approx. 80 to 86 kDa was detected. The cumulative mass fraction was in the range of 94 to 98% (species 1).

The high molecular weight fraction (species 2) eluting between 20 to 22 min showed a molecular mass in the range of 140 to 190 kDa. Due to the low Rayleigh signal intensity for high molecular weight fraction the molecular mass determined exhibited a higher degree of variation. The cumulative mass fraction of species 2 was in the range of 0.5 to 1% at a range between 120 to 200 kDa.

These results exhibit that OprF/I exists as a trimer (species 1) and that only a small portion of the protein forms aggregates of higher molecular mass (species 2).

The results obtained by SEC-MALS are also in good correlation with AUC results (see below). Results obtained by SEC/UV detection and native PAGE indicated higher molecular masses for the OprF/I fusion protein in the range of 180 kDa. Results obtained by SEC and native PAGE are based on the assumption of a globular protein shape, whereas the protein shape does not influence static light scattering or AUC data. Based on the results from the different methods that were applied, it was concluded that the OprF/I trimer does not exist in a globular shape but exhibits a large hydrodynamic radius.

Analytical Ultracentrifugation (AUC)

Sedimentation velocity profiles were recorded and deconvoluted with SedFit software to yield the sedimentation coefficient values of the sample components. The resulting calculated sedimentation coefficient and molecular mass for the individual species 1 (OprF/I fusion protein main peak) and species 2 (aggregates) were determined. The sedimentation coefficient values for the dominant component species 1 agree rather well for all samples studied. This indicates that no significant differences exist between the different samples examined. The molar mass of the main component species 1 differs within experimental variation for this parameter. It generally indicates a trimer of the OprF/I fusion protein. The molar masses of the monomer and trimer, as calculated from the sequence, are 24.1 kDa and 72.3 kDa, respectively.

Figure 8:
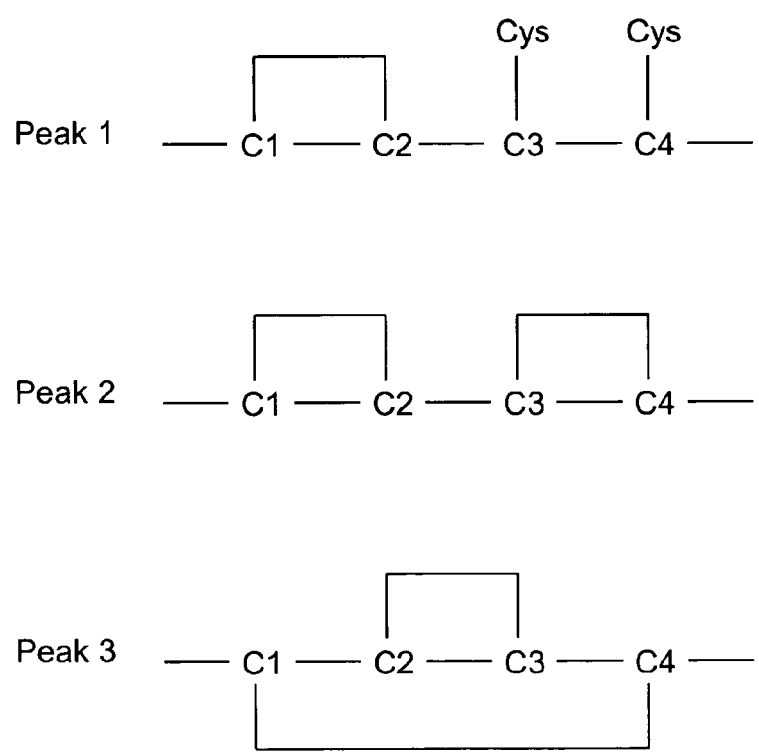
FIG. 8 shows the disulphide bond pattern of peaks P1, P2 and P3 of the OprF/I fusion protein.
Figure 9:
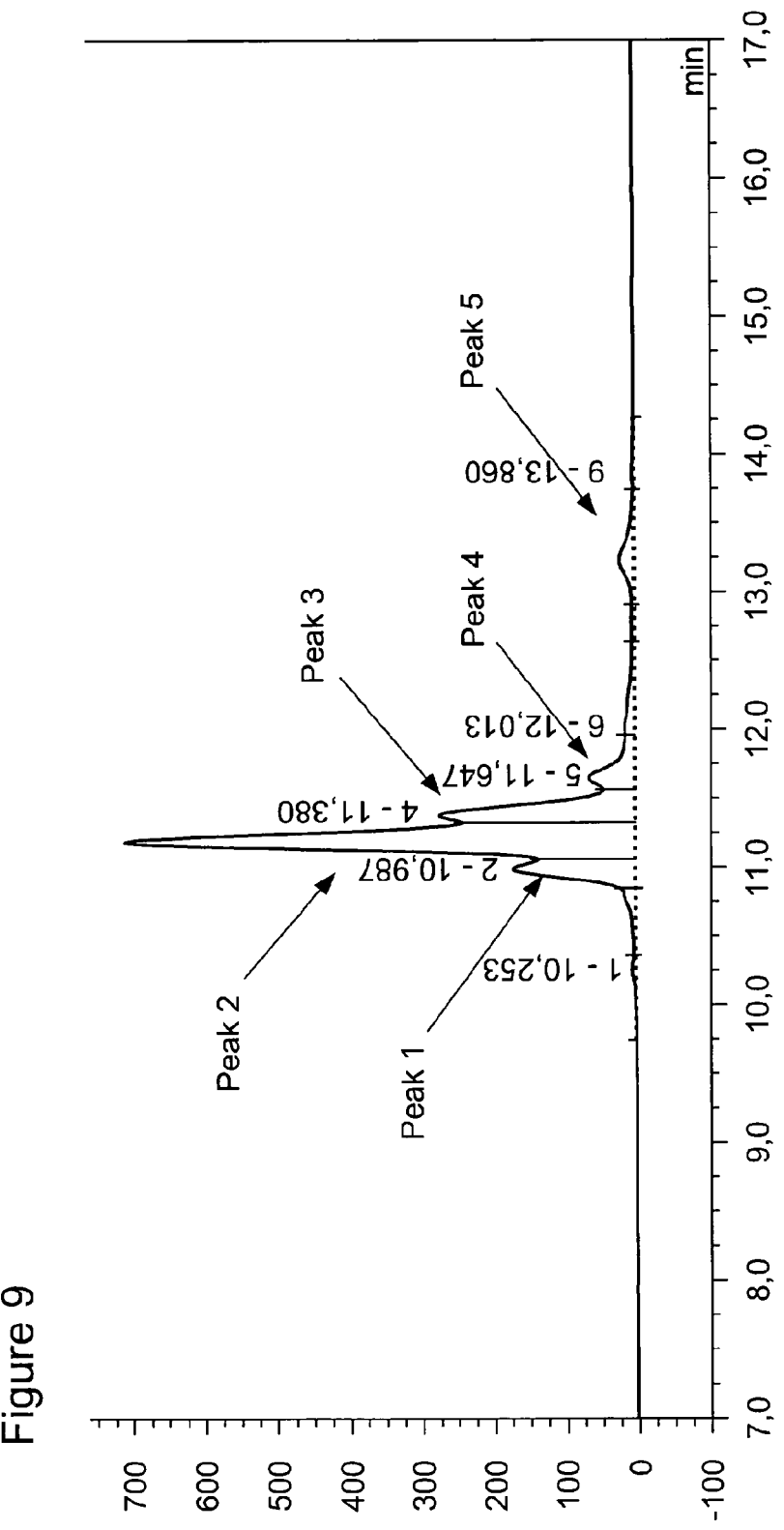
FIG. 9 shows the RP-HPLC peak pattern of purified OprF/I drug substance mixture.

No dissociation of this trimer occurred over the concentration range examined. The Stokes-radius for the trimer was calculated to be 5.6 nm. The Stokes-radius for a globular protein of the expected trimer mass is 2.8 nm. This indicates a highly asymmetrical and/or hydrated molecule. Species 2 appeared as a distinct peak at varying sedimentation coefficients. This indicates that species 2 corresponds to a component with a distinct stoichiometry (hexamer, nonamer, etc.), as opposed to unspecific aggregation. These data are in very good correlation to the SEC-MALS results showing that the native OprF/I fusion protein exists as a trimer, but are significantly different from the calculated molecular mass obtained by SEC and native PAGE (overestimation of mass due to non-globular shape). The primary and most reliable parameter from a sedimentation velocity experiment is the sedimentation coefficient itself. For the calculation of the SCD, a single frictional coefficient was assumed to apply for all sedimentation coefficients calculated. It was optimized in a fitting step. The frictional coefficient is necessary for the transformation of the SCD to a molar mass distribution (MMD). In the present study the signal for sedimentation coefficients <2 S only appeared at a ten-fold dilution. The possibility can be ruled that this peak corresponds to a putative monomer of OprF/I out because species 1 did not change. In conclusion, OprF/I is present in solution as a trimeric molecule. No dissociation occurred over the range of concentrations examined Disulfide Mapping Disulphide Bond Mapping Using Nano-MS/MS Analysis The aim of this study was to identify the differences in the disulphide bridge pattern between peaks 1, 2 and 3. The individual peaks were isolated and enriched. The primary sequence contains 4 cysteine residues at position 18 (C1), 27 (C2), 33 (C3) and 47 (C4) (see SEQ ID NO: 3). It was concluded from the data of the intact molecular weight determination by on-line LC/ES-MS that peak 1 has one disulphide bridge and two cysteinylations, and peaks 2 and 3 have two disulphide bridges. The tryptic digest of all three peaks produced the peptide fragment 1 to 55, which contains all four cysteines of the protein. The observed masses for this fragment in the three peaks confirmed the assignment from the intact MW analysis. The peptide fragment 1 to 55 from all three peaks were collected and subdigested with AspN and analysed by LC-MS. Based on the interpretation of the raw data the structures according to FIG. 8 were derived for the predominant component in the three different peaks.

These findings were confirmed by reduction and MS/MS experiments of selected signals from the AspN subdigest. In addition to the disulphide bridge pattern deamidation was observed in the three different peaks. In the tryptic peptide 120 to 132, the Asn 124 is probably partly deamidated. In different peptides, deamidation of Asn 45 was observed as well.

Influence of Temperature on Stability

SDS-PAGE gels (reducing and non-reducing conditions) were run for OprF/I fusion protein samples incubated at different temperatures over 10 days. Relative content of OprF/I fusion protein main band in reduced gels was calculated by densitometric evaluation of the gels by normalization of band intensities to 2-8° C. samples (reference). No degradation or changes in band pattern were observed for samples stored at −80° C., −20° C., 2-8° C. and RT (20° C.) over the storage period of 10 days.

Influence of pH on Stability

OprF/I fusion protein samples were incubated at different pH values at pH 1.98 to pH 11.1 and analyzed by RP-HPLC and SEC-HPLC. The main peak of the OprF/I fusion protein, which corresponds to the non-covalent trimer, was constant with approximately 90% at pH 5.9 to 11.1 over the storage period of at least 23 days at 2-8° C. The trimer reversibly dissociated at low pH (pH 2).

Aluminium Hydroxide as Additive/Adjuvant

RP-HPLC results showed that the OprF/I fusion protein could further be stabilized at pH 4.88 by binding onto aluminium hydroxide and could be desorbed at high recoveries.

Immunogenicity of Different OprF/I Fusion Protein Fractions (BALB/c Mouse Model)

Five BALB/c mice per group received 1 ml of different OprF/I fusion protein fractions (peaks 1, 2 and 3 of obtained from semi-preparative RP-HPLC fractions) and of the unfractionated OprF/I fusion protein (DS) i.p. at days 0 and 14. At day 21 the blood of the mice was tested for specific antibodies and the values (GMT [μg/ml]+SD) determined at specific doses (μg protein). The results are summarized in Table 3.

TABLE 3

| dose | Peak 1 | Peak 2 | Peak 3 | DS |
|---|---|---|---|---|
| 31.6 | 29.36 | 40.75 | 49.53 | 83.54 |
| 10 | 15.58 | 4.59 | 24.63 | 31.04 |
| 3.16 | 0.09 | 0.03 | 0.24 | 0.70 |
| 1 | 0.01 | 0.01 | 0.01 | 0.05 |
| 0.316 | 0.01 | 0.01 | 0.01 | 0.01 |

It was concluded that all fractions as well as the unfractionated OprF/I fusion protein induced specific antibodies. The ED50 value for the peak 2 fraction has additionally been determined as 5.6 μg (unfractionated OprF/I fusion protein: 1.8 μg).

CONCLUSIONS

1. The OprF/I fusion protein can be produced and purified without cross-linked disulfide aggregates in an over all yield up to 40% starting with the IMAC-Cu capture step (i.e. SEQ ID NO: 4 in the form of a trimer wherein trimer content of more than about 90% according to SEC and an aggregate content of less than 1%).
2. The OprF/I fusion protein (SEQ ID NO: 4) produced in different production lots is very consistent.
3. The OprF/I fusion protein (SEQ ID NO: 4) exists as a trimer under physiological conditions with a mean molecular mass of approximately 80 kDa and a relative content of 94 to 98%.
4. The OprF/I fusion protein (SEQ ID NO: 4) produced according to the present invention can be separated in several variants by RP-HPLC (see FIGS. 4 and 8) Peak 1 (P1) is a two-fold cysteinylated adduct at position 33 (C3) and 47 (C4) containing a disulphide bond between position 18 (C1) and 27 (C2) (see also SEQ ID NO: 4). Peak 2 (P2) is a variant containing two disulphide bridges at positions 18 (C1)-27 (C2) and 33 (C3)-47 (C4). Peak 3 (P3) is a further variant containing 2 disulphide bridges at positions 18 (C1)-48 (C4) and 27 (C2)-33 (C3).
5. The OprF/I fusion protein (SEQ ID NO: 4) is stable from −80° C. to +20° C. over a period of 10 days, and at pH 5.9 to 11.1 over a period of 23 days at 2-8° C. Furthermore (data not shown), the OprF/I fusion protein (SEQ ID NO: 4) is stable up to 24 months at 2 to 8° C. in PBS. At pH 4.88 the OprF/I fusion protein can be further stabilized by binding onto aluminium hydroxide.
6. All three variants (peaks 1, 2 and 3) as well as the unfractionated OprF/I fusion protein induced specific antibodies after vaccination of BALB/c mice.

Preferred Aspects

1. An OprF/I fusion protein comprising a portion of the *Pseudomonas aeruginosa* outer membrane protein F which is fused with its carboxy terminal end to a portion of the amino terminal end of the *Pseudomonas aeruginosa* outer membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, and further wherein said fusion protein contains a disulphide bond pattern, preferably selected from the group consisting of (a) Cys18-Cys27-bond (SEQ ID NO: 9), (b) Cys18-Cys27-bond and Cys33-Cys47-bond (SEQ ID NO: 10), and (c) Cys18-Cys47-bond and Cys27-Cys33-bond (SEQ ID NO: 11), or an immunogenic variant thereof having at least 85%, preferably 90%, in particular 95% identity to the amino acid sequence of SEQ ID NO: 4, and the same disulphide bond pattern as specified.
2. The OprF/I fusion protein according to aspect 1, wherein said fusion protein is trimeric.
3. The OprF/I fusion protein according to aspect 1 or 2, wherein said fusion protein further contains 1-24 amino acids fused to its amino terminal end, preferably selected from the group consisting of Met-, Met-Ala-(His)$_6$- (SEQ ID NO: 5), Ala-(His)$_6$- (SEQ ID NO: 6), Met-Lys-Lys-Thr-Ala-Ile-Ala-Ile-Ala-Val-Ala-Leu-Ala-Gly-Phe-Ala-Thr-Val-Ala-Gln-Ala- (SEQ ID NO: 7), Met-Lys-Leu-Lys-Asn-Thr-Leu-Gly-Val-Val-Ile-Gly-Ser-Leu-Val-Ala-Ala-Ser-Ala-Met-Asn-Ala-Phe-Ala- (SEQ ID NO: 8), in particular Ala-(His)$_6$- (SEQ ID NO: 6).

4. An OprF/I fusion protein mixture or complex containing or consisting essentially of three OprF/I fusion proteins according to aspect 1 or 3, in particular in the form of a trimer.
5. The OprF/I fusion protein mixture or complex according to aspect 4, said mixture or complex containing or consisting essentially of
   (a) an OprF/I fusion protein having only a Cys18-Cys27-bond (SEQ ID NO: 9),
   (b) an OprF/I fusion protein having a Cys18-Cys27-bond and a Cys33-Cys47-bond (SEQ ID NO: 10), and/or
   (c) an OprF/I fusion protein having a Cys18-Cys47-bond and a Cys27-Cys33-bond (SEQ ID NO: 11).
6. The OprF/I fusion protein mixture or complex according to aspect 5, wherein the relative distribution of the components are for component (a) about 15% to about 18%, preferably about 16%; for component (b) about 67% to about 62%, preferably about 66%; and for component (c) about 18% to about 20%, preferably about 18%.
7. The OprF/I fusion protein mixture or complex according to aspect 5 or 6, wherein the total relative content of all components (a) to (c) compared to the total protein content is at least 75%, preferably at least about 80% to about 90%, in particular at least about 85%.
8. The OprF/I fusion protein mixture or complex according to any of aspects 5-7, wherein each of the OprF/I fusion proteins contains an Ala-(His)$_6$-N-terminus, said mixture containing or consisting essentially of, in particular in the form of a trimer,
   (a) an OprF/I fusion protein having only a Cys18-Cys27-bond (SEQ ID NO: 9),
   (b) an OprF/I fusion protein having a Cys18-Cys27-bond and a Cys33-Cys47-bond (SEQ ID NO: 10), and/or
   (c) an OprF/I fusion protein having a Cys18-Cys47-bond and a Cys27-Cys33-bond (SEQ ID NO: 11).
9. A trimeric OprF/I fusion protein comprising a portion of the *Pseudomonas aeruginosa* outer membrane protein F which is fused with its carboxy terminal end to a portion of the amino terminal end of the *Pseudomonas aeruginosa* out membrane protein I, wherein said portion of the *Pseudomonas aeruginosa* outer membrane protein F comprises the amino acids 190-342 of SEQ ID NO: 1 and wherein said portion of the *Pseudomonas aeruginosa* outer membrane protein I comprises the amino acids 21-83 of SEQ ID NO: 2, or an immunogenic variant thereof having at least 85%, preferably 90%, in particular 95% identity to the amino acid sequence of SEQ ID NO: 3.
10. The trimeric OprF/I fusion protein according to aspect 9, wherein said fusion protein further contains 1-24 amino acids fused to its amino terminal end, preferably selected from the group consisting of Met-, Met-Ala-(His)$_6$- (SEQ ID NO: 5), Ala-(His)$_6$- (SEQ ID NO: 6), Met-Lys-Lys-Thr-Ala-Ile-Ala-Ile-Ala-Val-Ala-Leu-Ala-Gly-Phe-Ala-Thr-Val-Ala-Gln-Ala- (SEQ ID NO: 7), Met-Lys-Leu-Lys-Asn-Thr-Leu-Gly-Val-Val-Ile-Gly-Ser-Leu-Val-Ala-Ala-Ser-Ala-Met-Asn-Ala-Phe-Ala- (SEQ ID NO: 8), in particular Ala-(His)$_6$- (SEQ ID NO: 6).
11. A method for producing the OprF/I fusion protein according to any of aspects 1-10, said method comprising the steps of
    (a) reducing said OprF/I fusion protein with a reducing agent, preferably dithiothreitol (DTT), dithioerythritol (DTE) or β-mercaptoethanol, and
    (b) oxidizing the reduced OprF/I fusion protein with a redox agent, preferably the redox agent glutathione disulfide/glutathione or the redox agent cystine/cysteine, in the presence of a reducing agent, preferably dithiothreitol (DTT), dithioerythritol (DTE) or β-mercaptoethanol.
12. The method according to aspect 11, wherein in step (a) the concentration of the reducing agent is from about 3 mM to about 10 mM, preferably from about 3 mM to about 6 mM.
13. The method according to aspect 11 or 12, wherein in step (b) the concentration of the redox agent is from about 0.2 mM to about 4 mM, preferably about 0.2 mM to about 1 mM, in particular about 0.2 mM to about 0.5 mM, and the concentration of the reducing agent is from about 0.5 mM to about 1.5 mM, preferably about 1 mM.
14. The method according to any of the aspects 11 to 13, wherein the reaction temperature is from about 18° C. to about 25° C., preferably at about 20° C.
15. The method according to any of the aspects 11 to 14, wherein the reaction time of the reduction step (a) is from about 15 minutes to about 2 hours, preferably from about 30 minutes to about 1 hour, in particular about 30 minutes, and/or the pH value is from about 7.0 to about 8.5, in particular about 8.0.
16. The method according to any of the aspects 11 to 15, wherein the reaction time of the oxidation step (b) is from about 1 hour to about 20 hours, preferably from about 1 hour to about 6 hours, in particular from about 1.5 hours to about 2 hours, and/or the pH value is from about 7.5 to about 8.5, in particular about 8.0.
17. The method according to any of the aspects 11 to 16, wherein the reoxidized OprF/I fusion protein is further purified by an anion exchange chromatography, preferably Diethylaminoethyl- (DEAE-), Diethyl-(2-hydroxypropyl)aminoethyl- (QAE-) or Trimethylaminomethyl- (Q-) exchange chromatography, preferably DEAE- and/or Q-exchange chromatography, in particular wherein the reoxidized OprF/I-fusion protein is sequentially purified by DEAE- and Q-exchange chromatography, preferably by DEAE Sepharose® and Q-Sepharose® chromatography.
18. The method according to any of the aspects 11 to 17, wherein prior to the reduction of the OprF/I fusion protein, the OprF/I fusion protein is purified by affinity chromatography, preferably by immunoaffinity or immobilized metal ion affinity chromatography, in particular by immobilized metal ion affinity chromatography.
19. A pharmaceutical composition, in particular a vaccine, comprising the OprF/I fusion protein according to any of the aspects 1 to 10 or obtained by the method according to any of the aspects 11 to 17, and optionally at least one additive or adjuvant, in particular aluminium hydroxide, preferably formulated in an isotonic phosphate buffer saline solution (pH 7.4).
20. An antibody or antibody derivative which specifically binds the OprF/I fusion protein according to any of the aspects 1 to 10 or obtained by the method according to any of the aspects 11 to 17.
21. A protein complex comprising three OprF/I fusion proteins of SEQ ID NO: 4 or an immunogenic variant thereof having at least 85%, preferably 90%, in particular 95% identity to the amino acid sequence of SEQ ID NO: 4.
22. A protein complex consisting at least 80%, preferably 85%, more preferably 90% of three OprF/I fusion proteins of SEQ ID NO: 4 or an immunogenic variant thereof having at least 85%, preferably 90%, in particular 95% identity to the amino acid sequence of SEQ ID NO: 4.
23. Complex of aspect 21 or 22, wherein the OprF/I fusion proteins are selected from the group consisting of
    (a) the OprF/I fusion protein of SEQ ID NO: 4 with a Cys18-Cys27-bond (SEQ ID NO: 9), and (b) the OprF/I fusion protein of SEQ ID NO: 4 with a Cys18-Cys27-bond and Cys33-Cys47-bond (SEQ ID NO: 10), and
(c) the OprF/I fusion protein of SEQ ID NO: 4 with a Cys18-Cys47-bond and Cys27-Cys33-bond (SEQ ID NO: 11),
or an immunogenic variant thereof having at least 85%, preferably 90%, in particular 95% identity to the amino acid sequence of SEQ ID NO: 4, and the same disulphide bond pattern as specified in (a), (b) or (c).

24. Complex of aspect 23, wherein the complex consists of a) about 15% to about 18% of the OprF/I fusion protein of SEQ ID NO: 4 with a Cys18-Cys27-bond (SEQ ID NO: 9), b) about 62% to 67% of the OprF/I fusion protein of SEQ ID NO: 4 with a Cys18-Cys27-bond and Cys33-Cys47-bond (SEQ ID NO: 10), and c) about 18% to about 20% the OprF/I fusion protein of SEQ ID NO: 4 with a Cys18-Cys47-bond and Cys27-Cys33-bond (SEQ ID NO: 11).

25. Complex of aspect 23, wherein the sum of a) the OprF/I fusion protein of SEQ ID NO: 4 with a Cys18-Cys27-bond (SEQ ID NO: 9), b) the OprF/I fusion protein of SEQ ID NO: 4 with a Cys18-Cys27-bond and Cys33-Cys47-bond (SEQ ID NO: 10), and c) the OprF/I fusion protein of SEQ ID NO: 4 with a Cys18-Cys47-bond and Cys27-Cys33-bond (SEQ ID NO: 11) is equal or greater than 75%.

26. Complex of aspect 21 or 22, wherein the OprF/I fusion proteins are selected from the group consisting of
(a) the OprF/I fusion protein of SEQ ID NO: 4 with a Cys18-Cys27-bond (SEQ ID NO: 9), or
(b) the OprF/I fusion protein of SEQ ID NO: 4 with a Cys18-Cys27-bond and Cys33-Cys47-bond (SEQ ID NO: 10), or
(c) the OprF/I fusion protein of SEQ ID NO: 4 with a Cys18-Cys47-bond and Cys27-Cys33-bond (SEQ ID NO: 11),
or an immunogenic variant thereof having at least 85%, preferably 90%, in particular 95% identity to the amino acid sequence of SEQ ID NO: 4, and the same disulphide bond pattern as specified in (a), (b) or (c).

27. Complex of aspect 21 or 22, wherein the OprF/I fusion proteins is the OprF/I fusion protein of SEQ ID NO: 4 with a Cys18-Cys27-bond (SEQ ID NO: 9) or an immunogenic variant thereof having at least 85%, preferably 90%, in particular 95% identity to the amino acid sequence of SEQ ID NO: 4, and the same disulphide bond pattern as specified in SEQ ID NO: 9.

28. Complex of aspect 21 or 22, wherein the OprF/I fusion protein is the OprF/I fusion protein of SEQ ID NO: 4 with a Cys18-Cys27-bond and Cys33-Cys47-bond (SEQ ID NO: 10) or an immunogenic variant thereof having at least 85%, preferably 90%, in particular 95% identity to the amino acid sequence of SEQ ID NO: 4, and the same disulphide bond pattern as specified in SEQ ID NO: 10.

29. Complex of aspect 21 or 22, wherein the OprF/I fusion protein is the OprF/I fusion protein of SEQ ID NO: 4 with a Cys18-Cys47-bond and Cys27-Cys33-bond (SEQ ID NO: 11) or an immunogenic variant thereof having at least 85%, preferably 90%, in particular 95% identity to the amino acid sequence of SEQ ID NO: 4, and the same disulphide bond pattern as specified in SEQ ID NO: 11.

30. A pharmaceutical composition, in particular a vaccine, comprising the protein complex according to any of the aspects 21 to 29 or the protein complex obtained by the method according to any of the aspects 11 to 17, and optionally at least one additive or adjuvant, in particular aluminium hydroxide, preferably formulated in an isotonic phosphate buffer saline solution (pH 7.4).

31. An antibody or antibody derivative which specifically binds the protein complex according to any of the aspects 21 to 29 or the protein complex obtained by the method according to any of the aspects 11 to 17.

32. The antibody or antibody derivative of aspect 31, wherein said antibody or antibody derivative selectively binds to the protein complex according to any of the aspects 21 to 29 or the protein complex obtained by the method according to any of the aspects 11 to 17.

33. The antibody or antibody derivative of aspect 31, wherein said antibody or antibody derivative binds to a) the protein complex according to any of the aspects 21 to 29 or b) the protein complex obtained by the method according to any of the aspects 11 to 17 but does not bind to a monomer of the OprF/I fusion protein according to aspects 1 to 3.

34. A pharmaceutical composition comprising the antibody or antibody derivative according to aspects 32 or 33, and optionally pharmaceutically acceptable excipients.

35. The antibody or antibody derivative according to aspects 32 or 33 for use as a medicament, preferably for use in the reduction of mortality.

The invention claimed is:

1. A protein complex comprising a mixture of three OprF/I fusion proteins, wherein the OprF/I fusion proteins comprise
   (a) the OprF/I fusion protein of SEQ ID NO: 4 with a Cys18-Cys27-bond (SEQ ID NO: 9),
   (b) the OprF/I fusion protein of SEQ ID NO: 4 with a Cys18-Cys27-bond and Cys33-Cys47-bond (SEQ ID NO: 10), and
   (c) the OprF/I fusion protein of SEQ ID NO: 4 with a Cys18-Cys47-bond and Cys27-Cys33-bond (SEQ ID NO: 11).

2. The complex of claim 1, wherein at least 75% of the OprF/I fusion proteins in the mixture comprise (a) the OprF/I fusion protein with a Cys18-Cys27-bond (SEQ ID NO: 9), (b) the OprF/I fusion protein with a Cys18-Cys27-bond and a Cys33-Cys47-bond (SEQ ID NO: 10) and (c) the OprF/I fusion protein of with a Cys18-Cys47-bond and a Cys27-Cys33-bond (SEQ ID NO: 11).

3. A method for producing an OprF/I fusion protein, said method comprising the steps of
   (a) reducing an OprF/I fusion protein with a reducing agent, and
   (b) oxidizing the reduced OprF/I fusion protein with a redox agent, in the presence of the reducing agent;
   wherein the OprF/I fusion protein is the OprF/I fusion protein of SEQ ID NO: 4 with a Cys18-Cys27-bond (SEQ ID NO: 9), the OprF/I fusion protein of SEQ ID NO: 4 with a Cys18-Cys27-bond and Cys33-Cys47-bond (SEQ ID NO: 10), or the OprF/I fusion protein of SEQ ID NO: 4 with a Cys18-Cys47-bond and Cys27-Cys33-bond (SEQ ID NO: 11).

4. The method according to claim 3, wherein the concentration of the reducing agent of step (a) is from about 3 mM to about 10 mM and the reducing agent is dithiothreitol (DTT), dithioerythritol (DTE) or β-mercaptoethanol.

5. The method according to claim 3, wherein the concentration of the redox agent of step (b) is from about 0.2 mM to about 4 mM; the redox agent is glutathione disulfide/glutathione or cystine/cysteine; the concentration of the reducing agent of step (b) is from about 0.375 mM to about 1.5 mM; and the reducing agent is dithiothreitol (DTT), dithioerythritol (DTE) or β-mercaptoethanol.

6. The method according to claim 3, wherein the reaction temperature is from about 18° C. to about 25° C.

7. A pharmaceutical composition, comprising the protein complex according to claim 1, and at least one additive or adjuvant.

8. The pharmaceutical composition according to claim 7, wherein the additive or adjuvant is aluminium hydroxide.

9. The pharmaceutical composition according to claim 7, wherein the pharmaceutical composition is formulated in an isotonic phosphate buffer saline solution at pH 7.4.

10. A vaccine, comprising the protein complex according to claim 1 and at least one additive or adjuvant.

11. The vaccine according to claim 10, wherein the additive or adjuvant is aluminium hydroxide.

12. The vaccine according to claim 10, wherein the vaccine is formulated in an isotonic phosphate buffer saline solution at pH 7.4.

* * * * *